US010233198B2

(12) United States Patent
Yu et al.

(10) Patent No.: US 10,233,198 B2
(45) Date of Patent: Mar. 19, 2019

(54) PRO-DRUGS OF NSAIAS WITH VERY HIGH SKIN AND MEMBRANES PENETRATION RATES AND THEIR NEW MEDICINAL USES

(71) Applicant: Techfields Pharma Co., Ltd., Suzhou, Jiangsu (CN)

(72) Inventors: Chongxi Yu, Plainfield, IL (US); Lina Xu, Shanghai (CN)

(73) Assignee: Techfields Pharma Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 15/165,803

(22) Filed: May 26, 2016

(65) Prior Publication Data

US 2016/0272653 A1 Sep. 22, 2016

Related U.S. Application Data

(62) Division of application No. 12/663,262, filed as application No. PCT/IB2007/052090 on Jun. 4, 2007, now Pat. No. 9,371,284.

(51) Int. Cl.
*C07D 211/22* (2006.01)
*C07D 205/04* (2006.01)
(Continued)

(52) U.S. Cl.
CPC ......... *C07D 513/04* (2013.01); *C07D 205/04* (2013.01); *C07D 211/22* (2013.01);
(Continued)

(58) Field of Classification Search
CPC .. C07D 211/22; C07D 205/04; C07D 487/04; C07D 413/12; C07D 513/04;
(Continued)

(56) References Cited

U.S. PATENT DOCUMENTS 1,815,802 A 7/1931 Schleicher et al.
2,370,114 A 2/1945 Klemme et al.
(Continued)

FOREIGN PATENT DOCUMENTS

AU 2004201178 A1 4/2004
CA 1246446 12/1988
(Continued)

OTHER PUBLICATIONS

Tammara et al., caplus an 1993:678489.*
(Continued)

*Primary Examiner* — Sun Jae Yoo
(74) *Attorney, Agent, or Firm* — Finnegan, Henderson, Farabow, Garrett & Dunner, LLP

(57) ABSTRACT

The novel positively charged pro-drugs of NSAIAs in the general formulas (1, 2a, 2b, 2c, or 2d) "Structure 1, 2a, 2b, 2c, or 2d" were designed and synthesized. The compounds of the general formulas (1, 2a, 2b, 2c, or 2d) "Structure 1, 2a, 2b, 2c, or 2d" indicated above can be prepared from metal salts, organic base salts, or immobilized base salts of NSAIAs with suitable halide compounds. The positively charged amino groups in the pro-drugs in this invention largely increase the solubility of the drugs in water and will bond to the negative charge on the phosphate head group of membrane. Thus, the local concentration of the outside of the membrane or skin will be very high and will facilitate the passage of these pro-drugs from a region of high concentration to a region of low concentration. This bonding will disturb the membrane a little bit and may make some room for the lipophilic portion of the pro-drug. When the molecules of membrane move, the membrane may "crack" a little bit due to the bonding of the pro-drug. This will let the pro-drug insert into the membrane. At pH 7.4, only about 99% of the amino group is protonated. When the amino group is not protonated, the bonding between the amino group of the pro-drug and the phosphate head group of the membrane will disassociate, and the pro-drug will enter the membrane completely. When the amino group of the pro-drug flips to the other side of the membrane and thus becomes protonated, then the pro-drug is pulled into the cytosol, a semi-liquid concentrated aqueous solution or suspension. These pro-drugs can be used for treating and preventing diabetes (type I or/and type II), abnormal blood glucose and lipid levels, stroke, heart attack, and other heart and vascular diseases Alzheimer's diseases, Parkinson's diseases and other neurodegenerative diseases, psoriasis, discoid lupus erythematosus, systemic lupus erythematosus (SLE), autoimmune hepatitis, multiple sclerosis (MS), and other autoimmune diseases, amyotrophic lateral sclerosis (ALS), oculopharyngeal muscular dystrophy (OPMD), and other muscle disorders, inflamed hemorrhoids, cryptitis, other inflammatory conditions of the anorectum, and pruritus ani, prostatitis, prostatocystitis, varicose veins, autoimmune liver inflammation, autoimmune kidney inflammation, vein inflammation and other inflammations, skin cancers, breast cancer, colon-rectum cancer, oral cancer, and other cancers, scars, abnormal vascular skin lesions, birthmarks, moles (nevi), skin tags, aging spots (liver spots), and other skin disorders. These pro-drugs can be administered transdermally without the help of skin penetration enhancers.

Structure 1

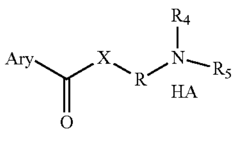

11 Claims, 1 Drawing Sheet

(51) Int. Cl.

| | |
|---|---|
| ***C07D 487/04*** | (2006.01) |
| ***C07D 413/12*** | (2006.01) |
| ***C07D 513/04*** | (2006.01) |
| ***C07D 409/12*** | (2006.01) |
| ***C07D 405/12*** | (2006.01) |
| ***C07D 403/12*** | (2006.01) |
| ***C07D 401/12*** | (2006.01) |
| ***C07D 417/12*** | (2006.01) |
| ***C07D 295/088*** | (2006.01) |
| ***C07D 491/052*** | (2006.01) |

(52) U.S. Cl.
CPC ....... *C07D 295/088* (2013.01); *C07D 401/12* (2013.01); *C07D 403/12* (2013.01); *C07D 405/12* (2013.01); *C07D 409/12* (2013.01); *C07D 413/12* (2013.01); *C07D 417/12* (2013.01); *C07D 487/04* (2013.01); *C07D 491/052* (2013.01)

(58) Field of Classification Search
CPC .. C07D 409/12; C07D 405/12; C07D 403/12; C07D 401/12; C07D 417/12
See application file for complete search history.

(56) References Cited

U.S. PATENT DOCUMENTS 2,671,805 A 3/1954 Krimmel et al.
3,365,483 A 1/1968 Jerzmanowska et al.
3,420,871 A 1/1969 Scherrer et al.
3,476,791 A 11/1969 Newman et al.
3,488,380 A 1/1970 Goldhamer et al.
3,679,672 A 7/1972 Yamamoto et al.
3,704,298 A 11/1972 Zinnes et al.
3,787,324 A 1/1974 Zinnes et al.
3,821,279 A 6/1974 Kurono et al.
3,822,258 A 7/1974 Zinnes et al.
3,956,363 A 5/1976 Shen et al.
3,957,764 A 5/1976 Lund
3,966,923 A 6/1976 Serre
4,006,181 A 2/1977 Cousse et al.
4,012,508 A 3/1977 Burton
4,035,376 A 7/1977 Janssen et al.
4,044,049 A 8/1977 Ruyle et al.
4,127,671 A 11/1978 Cognacq
4,146,637 A 3/1979 Metz et al.
4,150,137 A 4/1979 Noda et al.
4,180,662 A 12/1979 Pfister et al.
4,180,665 A 12/1979 Schwander et al.
4,206,220 A 6/1980 Sloan
4,207,332 A 6/1980 Hayashi et al.
4,244,948 A 1/1981 Boghosian et al.
4,346,709 A * 8/1982 Schmitt ................ A61K 9/0024 424/426
4,376,768 A 3/1983 Ozaki et al.
4,472,431 A 9/1984 Toth
4,543,353 A 9/1985 Faustini et al.
4,551,452 A 11/1985 Marfat
4,623,486 A 11/1986 Lombardino
4,640,689 A 2/1987 Sibalis
4,640,911 A 2/1987 Baschang et al.
4,689,338 A 8/1987 Gerster
4,743,704 A 5/1988 Nicolini
4,746,509 A 5/1988 Haggiage et al.
4,822,773 A 4/1989 Alexander et al.
5,081,118 A 1/1992 Braisted et al.
5,100,918 A 3/1992 Sunshine et al.
5,134,165 A 7/1992 Hirsch-Kauffmann
5,190,953 A 3/1993 Munson, Jr. et al.
5,192,753 A 3/1993 McGeer et al.
5,331,000 A 7/1994 Young et al.
5,399,562 A 3/1995 Becker et al.
5,570,559 A 11/1996 Lewis
5,604,259 A 2/1997 Jee
5,607,691 A 3/1997 Hale et al.
5,654,337 A 8/1997 Roentsch et al.
5,760,261 A 6/1998 Guttag
5,861,170 A 1/1999 Kissel
5,885,597 A 3/1999 Botknecht et al.
5,902,110 A 5/1999 Alfano et al.
6,011,049 A 1/2000 Whitcomb
6,054,457 A 4/2000 Setoi et al.
6,190,690 B1 2/2001 Park et al.
6,193,996 B1 2/2001 Effing et al.
6,262,121 B1 7/2001 Kawaji et al.
6,346,278 B1 2/2002 Macrides et al.
6,368,618 B1 4/2002 Jun et al.
6,416,772 B1 7/2002 Van Engelen et al.
6,444,234 B1 9/2002 Kirby et al.
6,528,040 B1 3/2003 Pearson et al.
6,592,891 B1 7/2003 Donati et al.
6,593,365 B1 7/2003 Yung-Yu Hung et al.
6,635,674 B1 10/2003 Kaneko et al.
6,638,528 B1 10/2003 Kanios
6,693,135 B2 2/2004 Yeager et al.
6,723,337 B1 4/2004 Song et al.
6,773,724 B2 8/2004 Franckowiak et al.
7,052,715 B2 5/2006 Fishman
7,256,210 B2 8/2007 Man et al.
2001/0038861 A1 11/2001 Hsu et al.
2003/0087962 A1 5/2003 Demopulos et al.
2004/0022837 A1 2/2004 Hsu et al.
2004/0229920 A1 11/2004 Garvey et al.
2004/0254182 A1 12/2004 Mulvihill et al.
2004/0266870 A1 12/2004 Allegretti et al.
2005/0037922 A1 2/2005 Bickers et al.
2005/0049255 A1 3/2005 Bictash et al.
2005/0080067 A1 4/2005 Allegretti et al.
2005/0107463 A1 5/2005 Woodward et al.
2005/0272108 A1 12/2005 Kalra et al.
2006/0003428 A1 1/2006 Tsai
2006/0024365 A1 2/2006 Vaya et al.
2006/0172002 A1 8/2006 Takada et al.
2007/0142607 A1 6/2007 Harasin et al.

FOREIGN PATENT DOCUMENTS

CA 2348741 A1 5/2000
CA 2614312 A1 1/2007
DE 1 944 758 3/1970
DE 2 909 642 5/1980
DE 3023206 A1 1/1982
EP 152379 A2 8/1985
EP 0202062 A2 11/1986
EP 237495 A2 9/1987
EP 289262 A2 11/1988
EP 0208404 B1 8/1990
EP 0469450 A1 2/1992
EP 659442 A1 6/1995
FR 5342 M 9/1967
FR 1593024 A 5/1970
FR 2410641 A1 6/1979
GB 585729 2/1947
GB 608492 9/1948
GB 851972 8/1960
GB 851972 10/1960
GB 958186 A 5/1964
GB 984471 2/1965
GB 1000208 8/1965
GB 1038725 8/1966
GB 1165300 9/1969
GB 1166861 10/1969
GB 1187259 A 4/1970
GB 2154585 A 9/1985
JP 52-78848 7/1977
JP 57-183738 11/1982
JP 57-183738 A 11/1982
JP A-H16-2004-517037 6/2004
JP 2004-525112 8/2004
JP 2005-504121 2/2005
WO WO 90/02141 A1 3/1990
WO WO 90/08128 7/1990
WO WO 93/07902 4/1993

(56) References Cited

FOREIGN PATENT DOCUMENTS

| | | | |
|---|---|---|---|
| WO | WO 93/14743 | A2 | 8/1993 |
| WO | WO 93/17677 | A1 | 9/1993 |
| WO | WO 93/25197 | | 12/1993 |
| WO | WO 93/25703 | A1 | 12/1993 |
| WO | WO 1994/00449 | | 1/1994 |
| WO | WO 1994/10167 | | 5/1994 |
| WO | WO 94/20635 | A1 | 9/1994 |
| WO | WO 95/34813 | | 12/1995 |
| WO | WO 1996/028144 | | 9/1996 |
| WO | WO 97/44020 | A1 | 11/1997 |
| WO | WO 97/45113 | A1 | 12/1997 |
| WO | WO 1998/040061 | | 9/1998 |
| WO | WO 98/47502 | A1 | 10/1998 |
| WO | WO 01/54481 | A2 | 8/2001 |
| WO | WO 01/58852 | A2 | 8/2001 |
| WO | WO 01/85143 | A2 | 11/2001 |
| WO | WO 2002/000167 | A2 | 1/2002 |
| WO | WO 02/68377 | A1 | 9/2002 |
| WO | WO 02/85297 | A2 | 10/2002 |
| WO | WO 2003/022270 | A1 | 3/2003 |
| WO | WO 03/29187 | A1 | 4/2003 |
| WO | WO 2003/061713 | A1 | 7/2003 |
| WO | WO 2004000300 | A1 | 12/2003 |
| WO | WO 2004004648 | A1 | 1/2004 |
| WO | WO 05/68421 | A1 | 7/2005 |
| WO | WO 05/97099 | A1 | 10/2005 |
| WO | WO 06/74249 | A1 | 7/2006 |
| WO | WO 2006/128184 | | 11/2006 |
| WO | WO 08/007171 | A1 | 1/2008 |
| WO | WO 08/010025 | A1 | 1/2008 |
| WO | WO 08/012602 | A1 | 1/2008 |
| WO | WO 08/012603 | A1 | 1/2008 |
| WO | WO 08/012605 | A1 | 1/2008 |
| WO | WO 08/017903 | A1 | 2/2008 |
| WO | WO 08/020270 | A1 | 2/2008 |
| WO | WO 08/029199 | A1 | 3/2008 |
| WO | WO 08/029200 | A1 | 3/2008 |
| WO | WO 2008/026776 | | 3/2008 |
| WO | WO 08/041054 | A1 | 4/2008 |
| WO | WO 08/041059 | A1 | 4/2008 |
| WO | WO 08/044095 | A1 | 4/2008 |
| WO | WO 08/056207 | A1 | 5/2008 |
| WO | WO 08/072032 | A1 | 6/2008 |
| WO | WO 08/087493 | A1 | 7/2008 |
| WO | WO 08/093173 | A1 | 8/2008 |
| WO | WO 08/149181 | A1 | 12/2008 |
| WO | WO 2008/012605 | A1 | 1/2009 |

OTHER PUBLICATIONS

Venuti et al.—abstract, 1990, caplus an 1990:111681.*
Venuti et al., Pharmaceutical Research, 1989, 6(10), 867-873.*
Kruse et al., 1997, caplus an 1997:752779.*
Foldeak et al., 1963, caplus an 1963:403366.*
Halen-et-al-full-reference, Chem. Biol. Drug Design, 2007, 70:450-455 (2007).*
Yu et al., 2009, caplus an 2009:1167480.*
Halen et al., 2007, caplus an 2007:1328517.*
Agawa, T., et al., "Stabilities of Vitamin A Urethans," Kogyo Kagaku Zasshi 58:686-688 (1955).
Allegretti, M. et al., "2-Arylpropionic CXC Chemokine Receptor 1 (CXCR1) Ligands as Novel Noncompetitive CXCL8 Inhibitors," J. Medic. Chem. 48(13):4312-4331 (2005).
Altuntas, T. G., et al., "A Study on the Interation Between p60c-src Receptor Tyrosine Kinase and Arylcarboxylic and Arylacetic Acid Derivatives Based on Docking Modes and In Vitro Activity," Biol. Pharm. Bull. 27(1 ):61-65 (2004).
Amin, R. C., et al., "Diethylaminoethyl Dialkylacetates," J. Amer. Pharma. Association 37:243-245 (1948).
Andrews, J. M., "Determination of Minimum Inhibitory Concentrations," Journal of Antimicrobial Chemotherapy 48, suppl. S1: 5-16 (2001).
Apt, L., et al., "A Randomized Clinical Trial of the Nonsteroidal Eyedrop Diclofenac After Strabismus Surgery," Ophthalmology 105:1448-1454 (1998).
Arora, P., et al., "Design Development, Physicochemical, and In Vitro and In Vivo Evaluation of Transdermal Patches Containing Diclofenac Diethylammonium Salt," J. Pharm. Sci. 91:2076-2089 (2002).
Barcia, E., et al., "Influence of Medium and Temperature on the Hydrolysis Kenetics of Propacetamol Hydrochloride: Determination Using Derivative Spectrophotometry," Chem. Pharm. Bull. 53(3):277-280 (2005).
Battaglino, R., et al., "Fluoxetine Treatment Increases Trabecular Bone Formation in Mice (Fluoxetine Affects Bone Mass)," J. Cell Biochem. 100(6):1387-1394 (2007).
Berge, S. M., et al., "Pharmaceutical Salts," J. Pharm. Sci. 66:1-19 (1977).
Brooks et al., caplus an 1996:350581.
Brown, K., et al., "Nonsteroidal Antiinflammatory Agents. 1,2,4-Diphenylthiazole-5-acetic Acid and Related Compounds," J. Med. Chem. 17(11):1177-1181 (1975).
Bundgaard, H., et al., "Prodrugs as Drug Delivery Systems IV: N-Mannich Bases as Potential Novel Prodrugs for Amides, Ureides, Amines, and Other NH-Acidic Compounds," J. Pharm. Sci. 69:44-46 (1980).
Campbell, C. L., et al., "Aspirin Dose for the Prevention of Cardiovascular Disease," JAMA 297(18):2018-2024 (2007).
Cannon, J. G., "Analog Design," Burger's Medicinal Chemistry and Drug Discovery, Ch. 19, 5th Ed., vol. 1: Principles and Practice, Wiley-Interscience, 1995, pp. 783-802.
Cevc, G., et al., "New, Highly Efficient Formulation of Diclofenac for the Topical, Transdermal Administration in Ultradeformable Drug Carriers, Transfersomes," Biochim. Biophys. Acta 1514:191-205 (2001).
Chanal, J. L., et al., "Etude de la Distribution et de L'Elimination Chez le Rat de L'Acetyl Salicylate de Dimethyl Amino Ethyle Influence de la Position du Marquage au Carbone 14," Boll. Chim. Farm. 119:331-338 (1980).
Cwalina, G. E., et al., "Synthesis and Stability Studies of Certain Disubstituted Aminoacetoxybenzoic Acids," J. Organic Chem. 26:3344-3346 (1961).
Dalpiaz, A., et al., "Vitamin C and 6-Amino-Vitamin C Conjugates of Diclofenac: Synthesis and Evaluation," International Journal of Pharmaceutics 291 (1-2):171-181 (2005).
D'Amour, F. E., et al., "A Method for Determining Loss of Pain Sensation," J. Pharmacol. Exp. Ther. 72:74-79 (1941).
Database Caplus [Online] Chemical Abstracts Service, Columbus, OH, US; "Esters of .Omega.-Aminoaliphatic Acids and p-Acetamidophenol," retrieved from STN database accession No. 1969:3537.
Diven, W. F., et al., "Treatment of Experimental Acute Otitis Media with Ibuprofen and Ampicillin," Int. J. Pediatric Otorhinolaryngology 33:127-139 (1995).
Drachman, D. B., et al.,"Cyclooxygenase 2 Inhibition Protects Motor Neurons and Prolongs Survival in a Transgenic Mouse Model of ALS," Ann. Neurol. 52:771-778 (2002).
Erlanson-Albertsson, C., et al., "Enterostatin—A Peptide Regulating Fat Intake," Obes. Rev. 5(4):360-372 (1997).
Faye, W. O., et al., Medicinal Chemistry, 4th Ed., Williams & Wilkins, p. 549.
Funt, L. S., "Oral Ibuprofen and Minocycline for the Treatment of Resistant Acne Vulgaris," J. Amer. Acad. Dermatol. 13(3):524-525 (1985).
Gamache, D.A., et al., "Nepafenac, A Unique Nonsteroidal Prodrug with Potential Utility in the Treatment of Trauma-Induced Ocular Inflammation: I. Asssessment of Anti-Inflammatory Efficacy," Inflammation 24(4):357-370 (2000).
Gidoh, M., et al., "Derivatives of Several Acidic Anti-Inflammatory Drugs Showing Local Anesthetic Effects and Their Possible Use in the Treatment of Leprous Neuritis," Nippon Rai Gakkai Zasshi 52(3):156-64 (1983).
Ginaldi, L., et al., "Osteoporosis, Inflammation and Ageing," Immunity & Ageing 2:14 (2005).

(56) References Cited

OTHER PUBLICATIONS

Giraud, I., et al., "Application to a Cartilage Targeting Strategy: Synthesis and In Vivo Biodistribution of 14C-Labeled Quaternary Ammonium-Glucosamine Conjugates," Bioconjugate Chem. 11:212-218 (2000).
Gossel, T.A., "Aspirin's Role in Reducing Cardiac Mortality," U.S. Pharmacitst, Feb. 1988, pp. 34-41.
Gringauz, A., "Certain Disubstituted O-Aminoacetoxy- and Propoxybenzoic and Cinnamic Acids and Their Tert-Butyl Esters," J. Pharma. Sci. 59(3):422-225 (1970).
Hacking, M.A.P.J., et al., "Lipase Catalysed Acylation of Hydroxylamine and Hydrazine Derivatives," Journal of Molecular Catalysis B: Exzymatic 11:315-321 (2001).
Halen, P. K., et al., "Combining Anticholinergic and Anti-Inflammatory Activities into a Single Moiety: A Novel Approach to Reduce Gastrointestinal Toxictiy of Ibuprofen and Ketoprofen," Chem. Biol. Drug Des. 70:450-455 (2007).
Halen, P. K., et al., "Synthesis and Pharmacological Evaluation of Some Dual-Acting Amino-Alcohol Ester Derivatives of Flurbiprofen and 2-[1,1'-Biphenyl-4-yl]Acetic Acid: A Potential Approach to Reduce Local Gastrointestinal Toxicity," Chemistry & Biodiversity 3(11): 1238-1248 (2006).
Hengesh, E. J., Principles of Medicinal Chemistry, 4th Ed., p. 591, Williams & Wilkins, 1995.
Hennekens, C. H., et al., "Final Report on the Aspirin Component of the Ongoing Physicians' Health Study," N. Eng. J. Med. 321:129-135 (1989).
Ho, et al., "The Percutaneous Penetration of Prostaglandin E1 and Its Alkyl Esters," Journal of Controlled Release 58:349 (1999).
Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).
Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).
In't Veld, B. A., et al., "Nonsteroidal Antiinflammatory Drugs and the Risk of Alzheimer's Disease," N. Eng. J. Med. 345(21 ):1515-1521 (2001).
Jona, J. A., et al., "Design of Novel Prodrugs for the Enhancement of the Transdermal Penetration of Indomethacin," International Journal of Pharmaceuticals 123:127-136 (1995).
Jung, Y. J., et al., "Colon-Specific Prodrugs of 5-Aminosalicylic Acid: Synthesis and In Vitro/In Vivo Properties of Acidic Amino Acid Derivatives of 5-Aminosalicylic Acid," J. Pharm. Sci. 90:1767-1775 (2001).
Kawathekar, N., et al., "Synthesis, Biological Evaluation and QSAR Analysis of Some New Derivatives of Ketoprofen and Flurbiprofen," Indian J. Pharmaceutical Sciences 60(6):346-352 (1998).
Kigasawa, K., et al., "Decomposition and Stabilization of Drugs. XVIII. Studies on the Stability of Carboxylic Acid Esters of Phenol and Their Effectiveness as Prodrug," J. Pharm. Soc. Japan 99(4):402-412 (1979).
Kisel, V.M., et al., "Condensed Isoquinolines. 15. Synthesis of 5,10-Dihydro[1,2,4]Triazolo[1,5-b]-Isoquinolines and Related Spiranes," Chemistry of Heterocyclic Compounds 38(10):1253-1262 (2002).
Knychalska-Karwan, Z., et al., "The Use of Edan in Stomatodynia," J. Stomatol. 38:10 (1985).
Kobayashi, M., et al., "A Model System for Convenient Fluorescent Labeling of Sugar Chain in Taka-Amylase A.," Biosci. Biotechnol. Biochem. 61 (11 ):1836-1839(1997).
Korean Intellectual Property Office, International Preliminary Report on Patentability for PCT/IB2006/052318 dated May 7, 2007.
Korean Intellectual Property Office, International Preliminary Report on Patentability for PCT/IB2006/052461 dated Mar. 29, 2007.
Korean Intellectual Property Office, International Preliminary Report on Patentability for PCT/IB2006/052549 dated Apr. 23, 2007.
Korean Intellectual Property Office, International Preliminary Report on Patentability for PCT/IB2006/052563 dated Apr. 25, 2007.
Korean Intellectual Property Office, International Preliminary Report on Patentability for PCT/IB2006/052575 dated Apr. 25, 2007.
Korean Intellectual Property Office, International Preliminary Report on Patentability for PCT/IB2006/053090 dated May 12, 2007.
Korean Intellectual Property Office, International Preliminary Report on Patentability for PCT/IB2006/053594 dated Jun. 20, 2007.
Korean Intellectual Property Office, International Preliminary Report on Patentability for PCT/IB2006/053619 dated Jun. 26, 2007.
Korean Intellectual Property Office, International Preliminary Report on Patentability for PCT/IB2006/053091 dated May 12, 2007.
Korean Intellectual Property Office, International Preliminary Report on Patetability for PCT/IB2007/052090 dated May 31, 2007.
Korean Intellectual Property Office, International Preliminary Report on Patentability for PCT/US2009/066884 dated Jun. 7, 2011.
Korean Intellectual Property Office, International Search Report for PCT/IB2006/052732 dated May 2, 2007.
Korean Intellectual Property Office, International Search Report for PCT/IB2006/052815 dated May 3, 2007.
Korean Intellectual Property Office, International Search Report for PCT/IB2006/053741 dated May 29, 2007.
Kovach, I. M., et al., "Amino Acid Esters of Phenols as Prodrugs: Synthesis and Stability of Glycine, beta-Aspartic Acid, and alpha-Aspartic Acid Esters of p-Acetamidophenol," J. Pharm. Sci. 70(8):881-885 (1981).
Machon, Z., et al., "Synthesis of Benzoylcholine Derivatives," Dissertationes Pharmaceuticae 17(4):491-496 (1965).
Madhu, C., et al., "Penetration of Natural Prostaglandins and Their Ester Prodrugs and Analogs Across Human Ocular Tissues in Vitro," Journal of Ocular Pharmacology 14(5):389-399 (1998).
Magnette, J.-L., et al., "Diclofenac Systemic Exposure is Not Increased when Topical Diclofenac is Applied to Ultraviolet-Induced Erythema," Eur. J. Clin. Pharmacol. 60:591-594 (2004).
McGeer, P.L., et al., "The Inflammatory Response System of Brain Implications for the Theray of Alzheimer and Other Neurodegenerative Diseases," Res. Rev. 21:195-218 (1995).
Milosovich, S., et al., "Testosteronyl-4-Dimethylaminobutyrate-HCI: A Prodrug with Improved Skin Penetration Rate," J. Pharm. Sci. 82(2):227-228 (1993).
Nebioglu, D., et al., "Synthesis and In Vitro Anti-Inflammatory Activities of Some New Diaryl Amine Derivatives as Prodrug of Diclofenac," J. Fac. Pharm. Gazi 10(1):69-81 (1993).
Nicolas, C., et al., "New Quaternary Ammonium Oxican Derivatives Targeted Toward Cartilage: Synthesis, Pharmacokinetic Studies, and Antiinflammatory Potency," J. Med. Chem. 42:5235-5240 (1999).
Nielsen, N. M., et al., "Evaluation of Glycolamide Esters and Various Other Esters of Aspirin as True Aspirin Prodrugs," J. Med. Chem. 32(3):727-734 (1989).
Non_steroidal_antiinflammatory_dr, 2011, http://en.wikipedia.org/wiki/Non-steroidal_anti-inflammatory_drug.
Ogino et al., 2002, caplus an 2002:51415.
Pan, D.S., et al., "Inhibitory Effect of Progesterone on Inflammatory Factors after Experimental Traumatic Brain Injury," Biomed. Environ. Sci. 20(5):432-438 (2007).
PDR Generics, "Fenoprofen Calcium," 1996, second edition, Medical Economics, Montvale, NJ, p. 1289-1292.
PDR Generics, "Ketoprofen," 1996, second edition, Medical Economics, Montvale, NJ, p. 1810-1815.
PDR Generics, 1996, 2nd Ed., Medical Economics, Montvale, New Jersey, p. 242-243.
Perioli, L., et al., "Potential Prodrugs of Non-Steroidal Anti-Inflammatory Agents for Targeted Drug Delivery to the CNS," European Journal of Medicinal Chemistry 39(8):715-727 (2004).
Ponte, C., et al., "Does Acetaminophen Interfere in the Antibiotic Treatment of Acute Otitis Media Caused by a Penicillin-Resistant Pneumococcus Strain? A Gerbil Model," Pediatric Res. 54(6):913-918 (2003).
Raisz, L., "Pathogenesis of Osteoporosis: Concepts, Conflicts, and Prospects," J. Clin. Invest. 115(12):3318-3325 (2005).
Rolka, D. B., et al., "Aspirin Use Among Adults with Diabetes," Diabetes Care 24(2):197-201 (2001).

(56) References Cited

OTHER PUBLICATIONS

Romundstad, L., et al., "Adding propacetamol to Ketorolac Increase the Tolerance to Painful Pressure," European Journal of Pain (Amsterdam, Netherlands) 10(3): 177-183, ISSN:1090-3801 (2006).
Roof, R.L., et al., "Gender Differences in Acute CNS Trauma and Stroke: Neuroprotective Effects of Estrogen and Progesterone," J. Neurotrauma 17(5):367-388 (2000).
Rosenberg, E.W., et al., "Effect of Topical Applications of Heavy Suspensions of Killed Malassezia Ovalis on Rabbit Skin," Mycopathologia 72:147-154 (1980).
Roth, H. J., et al., "Synthesis of Polymer Bound Antiphlogistic Agents," Archiv der Pharmazie 321(5):273-276 (1988).
Salimbeni, A., et al., "New Esters of N-Arylanthranilic Acids," Farmaco, Edizione Scientifica 30(4):276-286 (1975).
Santos, C., et al., "Cyclization-Activated Prodrug. Synthesis, Reactivity and Toxicity of Dipeptide Esters of Paracetamol," Bioorganic & Medicial Chemistry Letters 15(6):1595-1598 (2005).
Scott, I. L., "Keystone Symposia: Inflammation and Cancer, Breckenridge, CO, USA, Feb. 27-Mar. 3, 2005," Technical Reports 10(13)1-17.
Selim, A. S. M., et al., "A New Method for the Direct Isolation of Glycine from Protein Hydrolyzates," Biochemical Journal 61 (2): 177-179 (1955).
Shanbhag, V. R., et al., "Ester and Amide Prodrugs of Ibuprofen and Naproxen: Synthesis, Anti-Inflammatory Activity, and Gastrointestinal Toxicity," Journal of Pharmaceutical Sciences 81 (2):149-54 (1992).
Silverman, R.B., "The Organic Chemistry of Drug Design and Drug Action," Academic Press Inc. 1992, pp. 355-361.
Sloan, K. B., et al., "Design for Optimized Topical Delivery: Prodrugs and a Paradigm Change," Pharmaceutical Research 23(12):2729-2747 (2006).
Sloan, K. B., et al., "Designing for Topical Delivery: Prodrugs Can Make the Difference," Medicinal Research Reviews 23(6):763-793 (2003).
Soine, T. O., et al., "Antispasmodics. 1. Phenyl Esters of Beta-Dialkylaminopropionic Acids," J. Am. Pharm. Assoc. 41:236-238 (1952).
Song, N., et al., "Synthesis of a Derivative of Quaternary Ammonium-Ibuprofen," Journal of Ocean University of Qingdao 32(6):911-913 (2002).
Sorhede, M., et al., "Enterostatin: A Gut-Brain Peptide Regulating Fat Intake in Rat," J. Physiol. 87:273-275 (1993).
SpinalCordInjury, 2011, http://www.mayoclinic.com/health/spinal-cord-injury/DS00460/DSECTION=treatments-and-drugs.
Suzuki et al., 1976, caplus an 1976:43615.
Terry, M. B., et al., "Association of Frequency and Duration of Aspirin Use and Flormone Receptor Status With Breast Cancer Risk," JAMA 291 (21):2433-2489 (2004).
Thun, M.J., et al., "Aspirin Use and Reduced Risk of Fatal Colon Cancer," N. Eng. J. Med., 325(23):1593-1596 (1991).
Tjebbes, G.W.A., et al., "d-Ibuprofen in Ocular Inflammation Induced by Paracentesis of the Rabbit Eye," Prostaglandins, Butterworth, Stoneham, MA, US 40(1):29-33 (1990).
Toyooka et al., caplus an 1992:523750, 1992.
Tozkoparan, B., et al.,"6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).
Tute, M. S., et al., Principles of Medicinal Chemistry, Eds., Williams & Wilkins, Media, PA, 1995, pp. 52.
Urbanska, H., et al., "Synthesis and Pharmacological Properties of Aminoalkyl Esters of Nicotinic Acid Derivatives," Acta Poloniae Pharmaceutica 36(6):657-665 (1979).
Venuti, M. C., et al., "Synthesis and Biological Evaluation of Omega-(N,N,N-Trialkylammonium)Alkyl Esters and Thioesters of Carboxylic Acid Nonsteroidal Antiinflammatory Agents," Pharmaceutical Research 6(10):867-873 (1989).
Warolin, C., et al.,"Sur L'Activite Pharamacodynamique de LAnhydride Acetylsalicylique et du Chlorhydrate D'Acetylsalicylate de N Diethylaminoethyle (1)," Therapie 21(1):245-59 (1966).
Wiwattanawongsa, K., et al., "Experimental and Computational Studies of Epithelial Transport of Mefenamic Acid Ester Prodrugs," Pharmaceutical Research 22(5):721-727 (2005).
Wolinski, J., et al., "Search for Anticholinargic Compounds. XX. Synthesis of Aminoalkyl O-, M-, and P-Hydroxybenzoates and O-, M-, and P-Acetoxybenzoates," Acta Poloniae Pharmaceutica 37(3):275-280 (1980).
Woods, H. F., et al., "Inhibition by Salicylate of Gluconeogenesis in the Isolated Perfused Rat Liver," Clin. Exp. Pharmacol. Physiol. 1(6):535-540 (1974).
Wright, D.W., et al., "ProTECT: A Randomized Clinical Trial of Progesterone for Acute Traumatic Brain Injury," Ann. Emerg. Med. 49(4):391-402 (2007).
Xiao, G., et al., "Improved Outcomes from the Administration of Progesterone for Patients with Acute Severe traumatic brain injury: A Randomized Controlled Trial," Crit. Care 12:R61 (2008).
Yadav, M.R., et al., "Synthesis and Pharmacological Evaluation of Some Dual-Acting Aminoalcohol Ester Derivatives of Flurbiprofen and 2-[1,1'-Biphenyl-4-yl] Acetic Acid: A Potential Approach to Reduce Local Gastrointestinal Toxicity," Chem. & Biodiversity 3(11 ):1238-1248 (2006).
Yang et al., 2005, caplus an 2005:221029.
Yang, S., et al., "Specificity of RGS10A as a Key Component in the RANKL Signaling Mechanism for Osteoclast Differentiation," J. Cell Sci. 120:3362-3371 (2007).
Zovko, M., et al., "Macromolecular Prodrugs. IX. Synthesis of Polymer-Fenoprofen Conjugates," Int. J. Pharmaceutics 228:129-138 (2001).
Zovko, M., et al., "The Novel Ketoprofenamides: Synthesis and Spectroscopic Characterization," Croatica Chemica Acta 76(4):335-341 (2003).
Gould, P. L. "Salt Selection for Basic Drugs," International Journal of Pharmaceutics, 33: 201-217 (1986).
Rautio, et al., "Piperazinylalkyl prodrugs of naproxen improve in vitro skin permeation," European Journal of Pharmaceutical Sciences, 11, pp. 157-163 (2000).

* cited by examiner

PRO-DRUGS OF NSAIAS WITH VERY HIGH SKIN AND MEMBRANES PENETRATION RATES AND THEIR NEW MEDICINAL USES

TECHNICAL FIELD

The present invention relates to the design and preparation of positively charged and water-soluble pro-drugs of nonsteroidal anti-inflammatory agents (NSAIAs) with very high skin, scars, blood-milk, and brain-blood barriers penetration rates and their new medicinal uses in treating and preventing diabetes (type I & II), abnormal blood glucose and lipid levels, stroke, heart attack, and other heart and vascular diseases, Alzheimer's diseases, Parkinson's diseases and other neurodegenerative diseases, psoriasis, discoid lupus erythematosus, systemic lupus erythematosus (SLE), autoimmune hepatitis, scleroderma Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, and pulmonary fibrosis, multiple sclerosis (MS), Crohn's disease, and other autoimmune diseases, amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders, hemorrhoids, inflamed hemorrhoids, post irradiation (factitial) proctitis, chronic ulcerative colitis, cryptitis, other inflammatory conditions of the anorectum, and pruritus ani, prostatitis, prostatocystitis, varicose veins, autoimmune liver inflammation, autoimmune kidney inflammation, colon-rectum inflammation, intestine inflammation, vein inflammation, vascular inflammation, and other inflammations, skin cancers, breast cancer, colon-rectum cancer, oral cancer, lung and other respiratory system cancers, uterus cancer, genital cancer, urinary organs cancers, leukemia and other blood and lymph tissues cancers and other cancers, scars, abnormal vascular skin lesions, birthmarks, moles (nevi), skin tags, aging spots (liver spots), and other skin disorders. These pro-drugs can be administered transdermally without the help of skin penetration enhancers.

BACKGROUND ART

NSAIAs are used for the relief of signs and symptoms of rheumatoid arthritis, osteoarthritis and ankylosing spondylitis. NSAIAs are used alone or as an adjunct in the treatment of biliary colic, fever, and episiotomy pain. It is also used in treatment of gout, acute migraine headaches, and renal colic and in the treatment of postoperative inflammation in patients who have undergone cataract extraction. Aspirin is used for preventing heart and vascular diseases.

Unfortunately, a number of side effects are associated with the use of NSAIAs, most notably GI disturbances such as dyspepsia, gastroduodenal bleeding, gastric ulcerations, and gastritis. Fishman (Fishman; Robert, U.S. Pat. No. 7,052,715) indicated that an additional problem associated with oral medications, is that the concentration levels which must be achieved in the bloodstream must be significant in order to effectively treat distal areas of pain or inflammation. These levels are often much higher than would be necessary if it were possible to accurately target the particular site of pain or injury. Fishman and many others (Van Engelen et al. U.S. Pat. No. 6,416,772; Macrides at al. U.S. Pat. No. 6,346,278; Kirby et al. U.S. Pat. No. 6,444,234, Pearson et al. U.S. Pat. No. 6,528,040, and Botknecht et al. U.S. Pat. No. 5,885,597) have attempted to develop a delivery system for transdermal application by formulation. Song, et al. developed a transdermal drug delivery system for anti-inflammatory analgesic agent comprising of diclofenac diethylammonium salt (Song, et. al., U.S. Pat. No. 6,723,337). Donati, et al. developed a plaster for topical use containing heparin and diclofenac. (Donati, et al., U.S. Pat. No. 6,592,891). Kawaji, et al. developed an oily patch for external use containing diclofenac sodium (Kawaji, at al. U.S. Pat. No. 6,262,121). Effing, et al. developed a device for the transdermal delivery of diclofenac (Effing, et al. U.S. Pat. No. 6,193,996). It is very difficult, however, to deliver therapeutically effective plasma levels of NSAIAs into the host by formulation. Susan Milosovich, et. al. designed and prepared testosteronyl-4-dimethylaminobutyrate.HCl (TSBH), which has a lipophilic portion and a tertiary amine groups that exists in the protonated form at physiological pH. They found that the prodrug (TSBH) diffuses through human skin ~60 times faster than does the drug (TS) itself [Susan Milosovich, et al., J. Pharm. Sci., 82, 227(1993).

DISCLOSURE OF INVENTION

Technical Problem

Some NSAIAs have been used medicinally for more than 100 years. NSAIAs are indicated for the relief of the signs and symptoms of rheumatoid arthritis and osteoarthritis, the relief of mild to moderate pain, the reduction of fever, and the treatment of dysmenorrhea. They are the most widely used drugs in the world.

Unfortunately, a number of side effects are associated with the use of NSAIAs, most notably GI disturbances such as dyspepsia, heartburn, vomiting, gastroduodenal bleeding, gastric ulcerations, and gastritis. Gastroduodenal bleeding induced by NSAIAs is generally painless but can lead to fecal blood loss and may cause a persistent iron deficiency anemia.

Transdermal delivery systems help to avoid directly hurting the gastro-intestinal tract and inactivation of the drugs caused by the "first pass metabolism" in the gastro-intestinal tract and liver. Traditional transdermal drug delivery by using skin penetration enhancer has limits. First, the penetration rates are very low (in μg/cm$^2$/h scale). Second, large amounts of enhancer will enter the host body that may cause very serious side effects.

Technical Solution

Transdermal delivery systems help to avoid directly hurting the gastro-intestinal tract and inactivation of the drugs caused by the "first pass metabolism" in the gastro-intestinal tract and liver. Traditional transdermal drug delivery by using skin penetration enhancers has limits. First, the penetration rates are very low (in μg/in$^2$/h scale). Second, large amounts of enhancer will enter the host body and may cause extra side effects. Third, in traditional transdermal drug delivery by using skin penetration enhancers, the high concentrated enhancers in the formulation may help the drug cross the skin, but when the enhancers and drug enter the skin, the concentration of enhancers will be diluted greatly and they cannot provide any more help for drug molecule to cross more biologic membranes, and then the drug molecule will be accumulated in the fat layer under the skin and the accumulated drugs may cause very serious and even fatal side effects.

Biological availability of a drug is the measurement of the relative amount of administered drug that reaches the general circulation. However, the general circulation is not the "site of action" for most of drugs. Even if the drug molecules have reached the general circulation, they must cross more biologic membranes, which may be less permeable than the gastrointestinal membranes, and interact with intercellular and intracellular fluids before reaching the elusive region called the "site of action"; thus most drugs will be metabolized by intestinal mucosa, liver, blood, kidneys, and lungs before they reach the "site of action." The situation not only produces very low pharmacological effect, but also causes toxic burden on intestinal mucosa, blood, liver, kidneys, and lungs. If we can increase various membranes penetration rates of drugs, the pharmacological effect and the clinical response of drugs will be increased greatly, then a smaller drug dosage will be needed and fewer side effects will be caused. The transdermal pro-drug delivery for the pro-drugs with very high skin and membranes penetration rates will be very useful not only for local diseases, but also for systemic diseases. Because these prodrugs have tens or hundreds of times more potency than the parent drugs, only a few tenths or hundredths of the normal drug dosage is needed and much less side effects will be caused. This will benefit not only transdermal drug delivery, but also to any other drug delivery systems (such as oral, subcutaneous, intravenous, inhalation, and nasal).

We found that drugs that have a lipophilic portion and a primary, secondary, or tertiary amine group (preferably tertiary amine groups) that exists in the protonated form (hydrophilic portion) at physiological pH can penetrate skin, scar, blood-brain, and blood-milk barriers in very high rates (in $mg/cm^2/h$ scale). The principles for designing these prodrugs of NSAIAs are:

1. The prodrug must have a lipophilic portion and a primary, secondary, or tertiary amine group (preferably tertiary amine groups) that exists in the protonated form (hydrophilic portion) at physiological pH.
2. Every prodrug of NSAIAs should have only one or two (preferably one) primary, secondary, or tertiary amine groups that exist in the protonated form (hydrophilic portion) at physiological pH.
3. The main role of the primary, secondary, or tertiary amine group is to help the drug pass through the skin, scars, membrane, blood-brain, blood-milk, and other barriers. The primary, secondary, or tertiary amine group can be any structure that is non-toxic and does not interfere the parent drugs' biologic activities.

We have disclosed some of the pro-drugs of all NSAIAs that have the general formula (1) "Structure 1" in patents (international application Nos: PCT/IB2006/052732, PCT/IB2006/052318, PCT/IB2006/052815, PCT/IB2006/052563, PCT/IB2006/052575, PCT/IB2006/053741, PCT/IB2006/053091, PCT/IB2006/053090, PCT/IB2006/052549).

[Chem. 1]

Structure 1

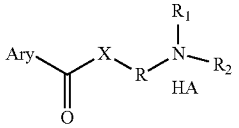

In which, R represents a branched or straight chain $-(CH_2)_n-$, n=0, 1, 2, 3, 4, 5, 6, 7, 8, 9, 10, 11, 12, . . . , in $-(CH_2)_n-$, any $CH_2$ may be replaced with O, S, $NR_8$, CH=CH, C≡C, $CHR_8$, $CR_8R_9$, aryl or heteroaryl residues, or any other moieties which are pharmaceutically acceptable; $R_1$ or $R_2$ represents H, one of any alkyl, alkyloxyl, alkenyl, perfluoroalkyl, alkyl halide or alkynyl residues having 1 to 12 carbon atoms, aryl or heteroaryl moieties, wherein, any $CH_2$ may be replaced with O, S, CH=CH, C≡C, $CHR_8$, $CR_8R_9$, aryl or heteroaryl moieties, or any other moieties which are pharmaceutically acceptable; X represents O, NH, $NR_8$, S, or none; $R_5$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties; $R_9$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties; HA represents none, HCl, HBr, HF, HI, HOAc, citric acid, or any acids which are pharmaceutically acceptable. All R, $R_1$, $R_2$, $R_8$, $R_9$ or $-(CH_2)_n-$ groups are branched or straight chains and may include C, H, O, Cl, Br, F, I, P, S, N or any other atoms which are pharmaceutically acceptable and may have single, double, or/and triple bonds; all R, $R_1$, $R_2$, $R_8$, $R_9$ or $-(CH_2)_n-$ groups may be achiral or chiral, if a group is chiral, it may have one or more chiral centers and may be a single (R) or (S) enantiomer or a mixture of (R) and (S) enantiomers; Ary- represents, but is not limited to:

[Chem. 2]

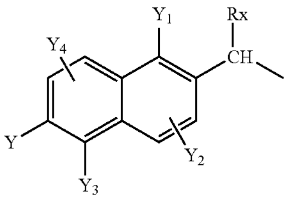

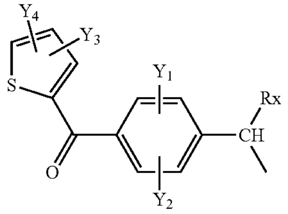

[Chem. 3]

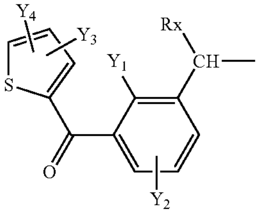

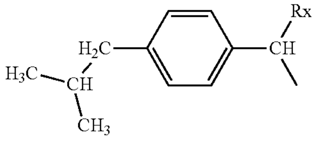

-continued
[Chem. 4]
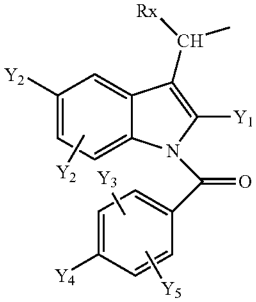
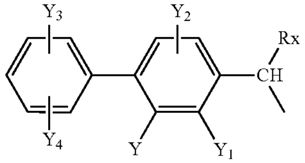
[Chem. 5]
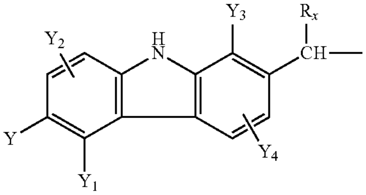
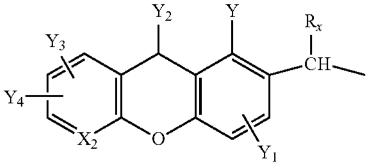
[Chem. 6]
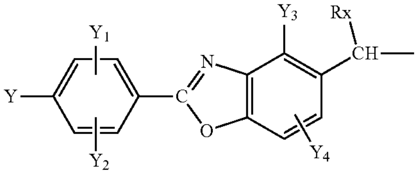
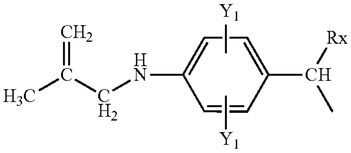
[Chem. 7]
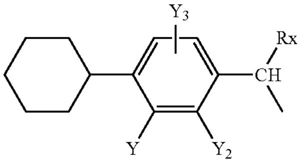
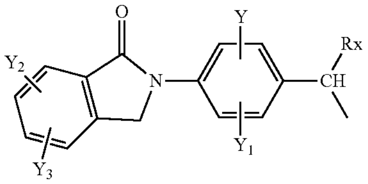
[Chem. 8]
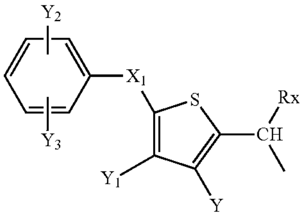
-continued
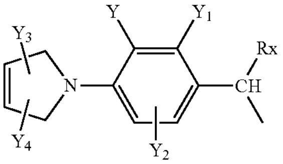
[Chem. 9]
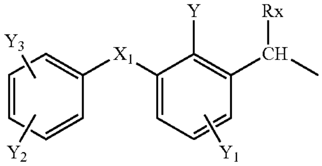
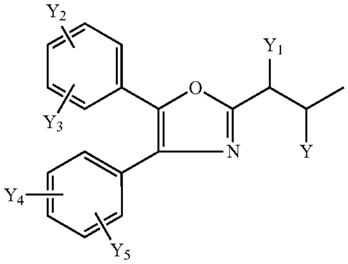
[Chem. 10]
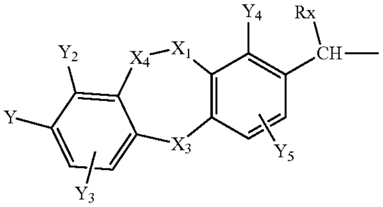
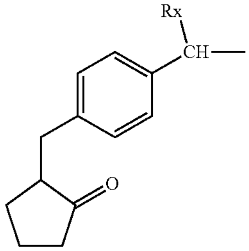
[Chem. 11]
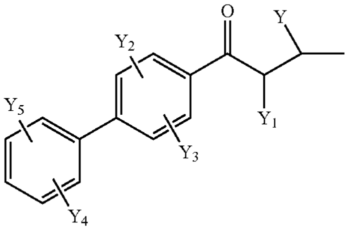
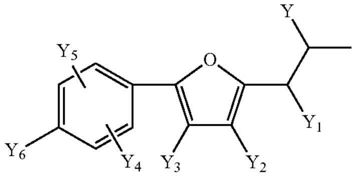

-continued
[Chem. 12]
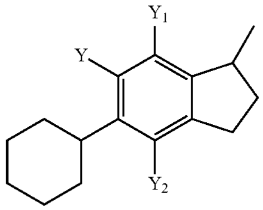
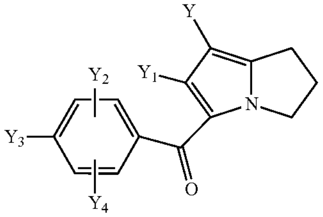
[Chem. 13]
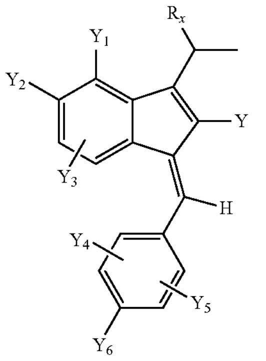
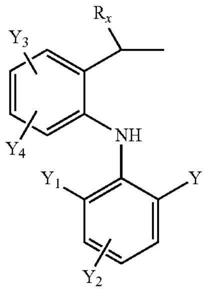
[Chem. 14]
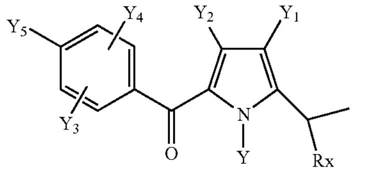
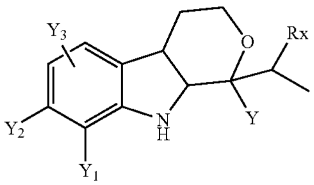
[Chem. 15]
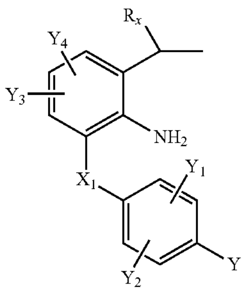
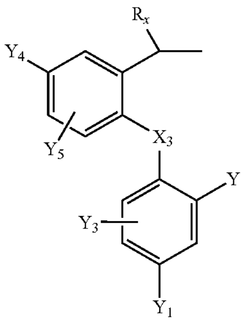
-continued
[Chem. 16]
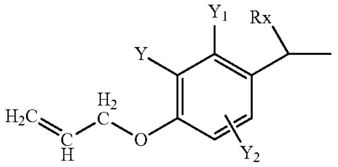
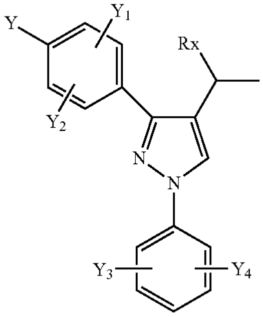
[Chem. 17]
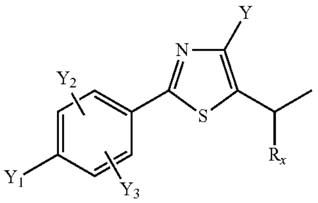
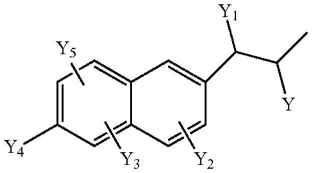
[Chem. 18]
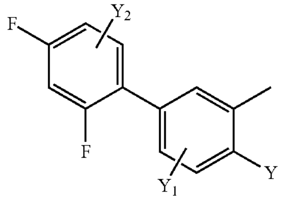
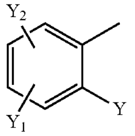
[Chem. 19]
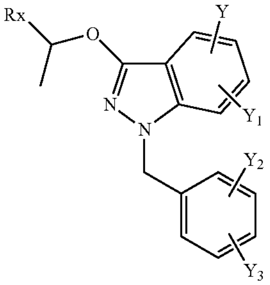
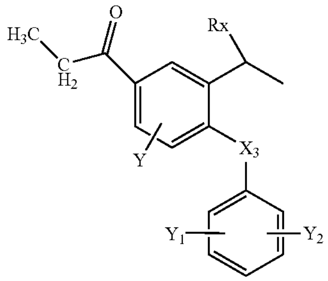

-continued
[Chem. 20]
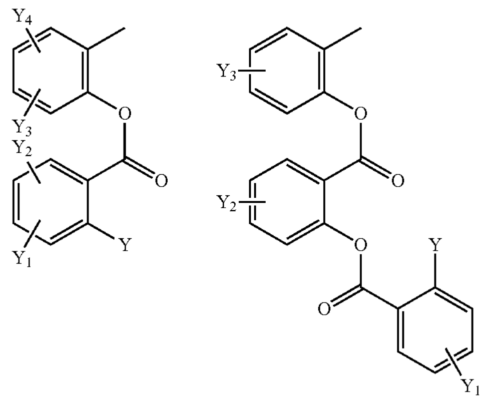
[Chem. 21]
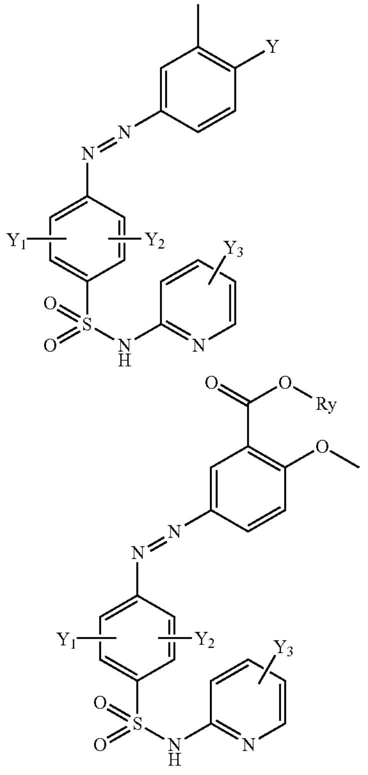
[Chem. 22]
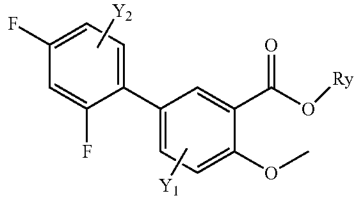
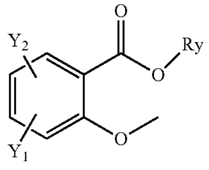
-continued
[Chem. 23]
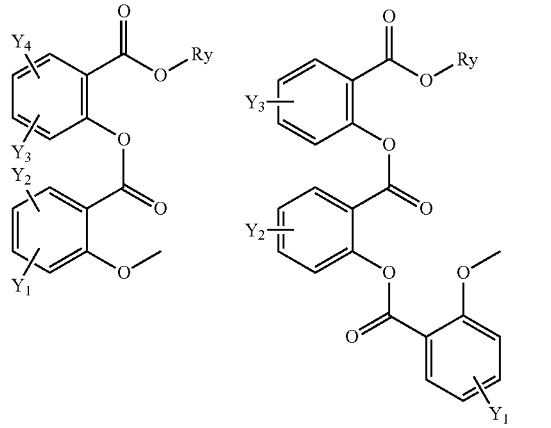
[Chem. 24]
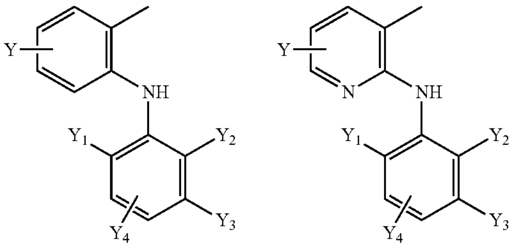
[Chem. 25]
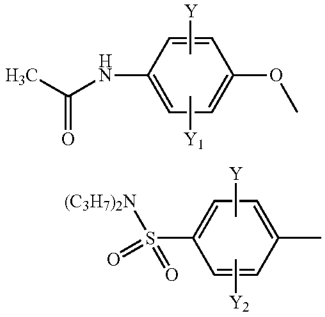
[Chem. 26]
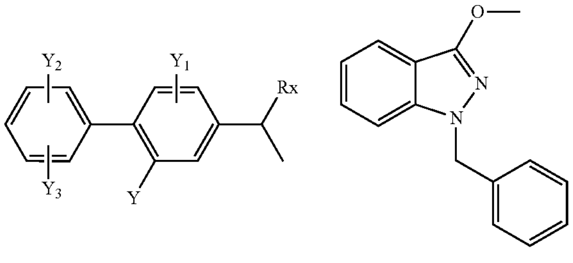
[Chem. 27]
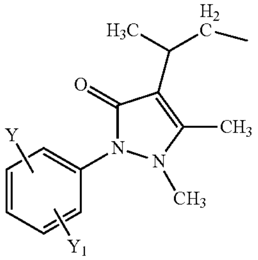

-continued
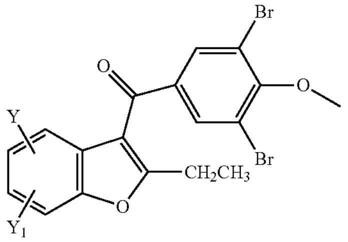
[Chem. 28]
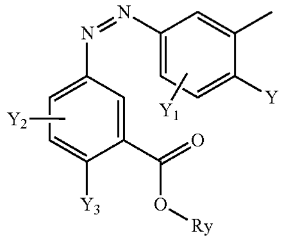
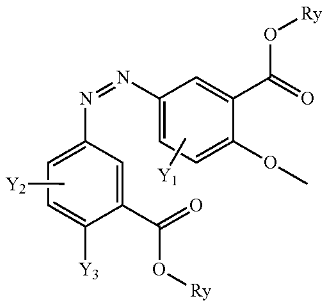
[Chem. 29]
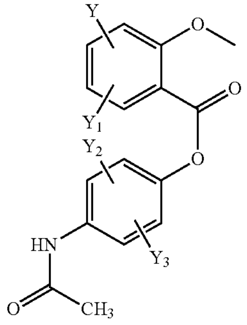
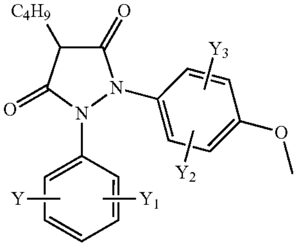
[Chem. 30]
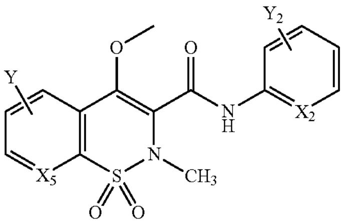
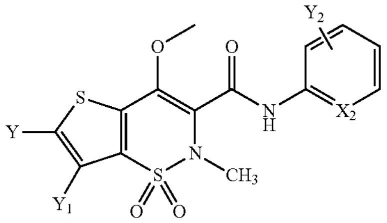
-continued
[Chem. 31]
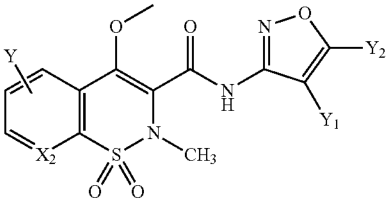
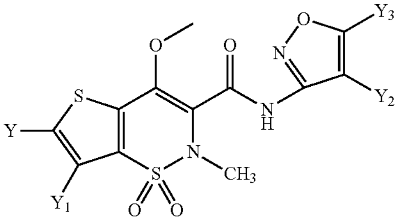
[Chem. 32]
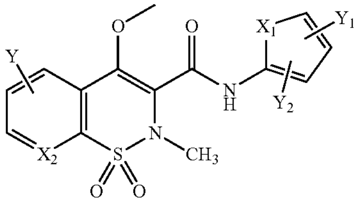
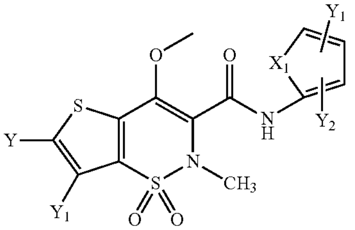
[Chem. 33]
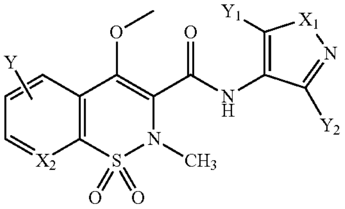
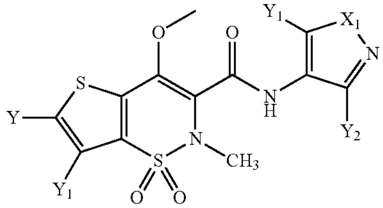
[Chem. 34]
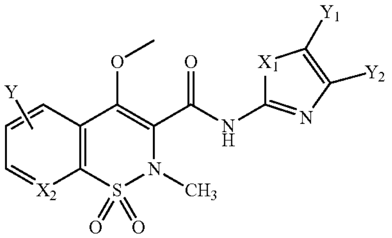

-continued

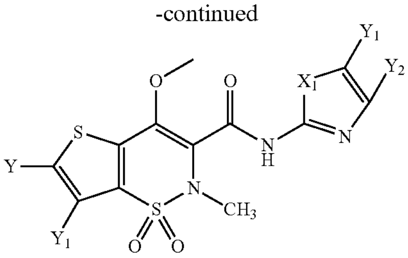

[Chem. 35]

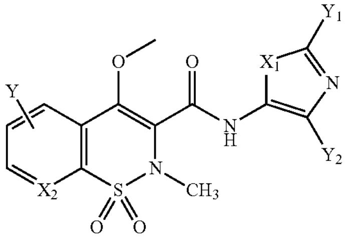

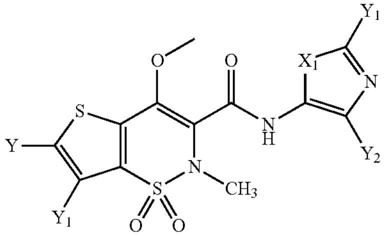

[Chem. 36]

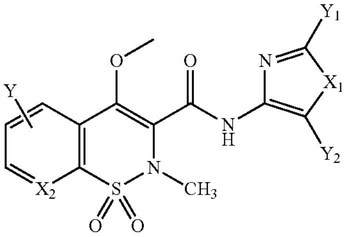

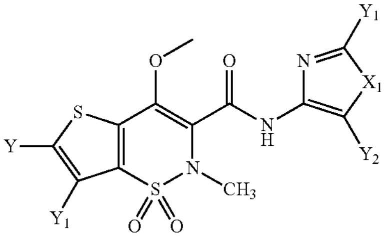

[Chem. 37]

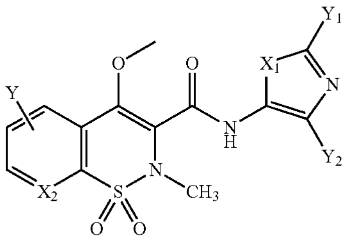

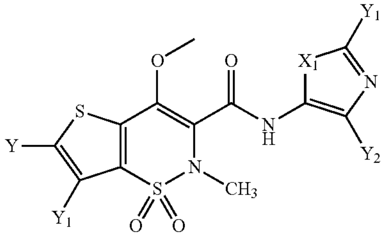

-continued

[Chem. 38]

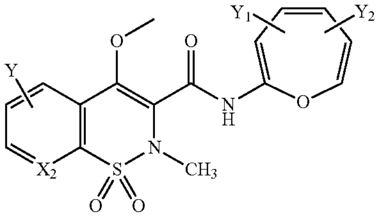

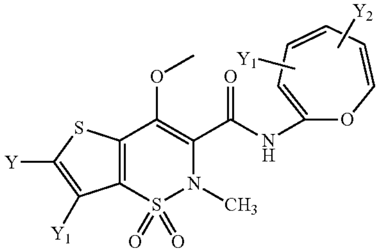

wherein, $R_x$ represents H, $CH_3$, $CH_3O$, OH, $CH_3CH_2$, $CF_3$, $CHF_2$, $CH_2F$, Cl, F, Br, F; $R_y$ represents H, one of any alkyl, alkyloxyl, alkenyl, perfluoroalkyl, alkyl halide or alkynyl residues having 1 to 12 carbon atoms, aryl or heteroaryl moieties; $X_1$ or $X_4$ represents $CH_2$, S, O, NH, or CO; $X_2$ or $X_5$ represents CH, $CR_8$, or N; $X_3$ represents O, S, NH, or $NR_8$; Y, $Y_1$, $Y_2$, $Y_3$, $Y_4$, $Y_5$, $Y_6$ represents independently H, HO, $CH_3COO$, $R_yCOO$, HS, $NO_2$, CN, $CH_3$, COS, $NH_2$, $CH_3CONH$, $R_yCONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_ySO_2$, $CH_3SO$, $R_ySO$, CH3CO, $CH_3CH_2CO$; any Ary- may be achiral or chiral; If a Ary- is chiral, it may have one or more chiral centers and may be a single (R) or (S) enantiomer or a mixture of (R) and (S) enantiomers.

We found that the role of the primary, secondary, or tertiary amine group is only to help the drug pass through the skin, membrane, blood-brain, blood-milk, and other bathers, so the primary, secondary, or tertiary amine group can be any kind of structures which are non-toxic and do not interfere the parent drugs' biologic activities. So we designed and prepared different kinds of amines groups for this property. The new pro-drugs of NSAIAs have the general formulas (2a, 2b, 2c, or 2d) "Structure 2a, 2b, 2e, or 2d"

[Chem. 39]

Structure 2a

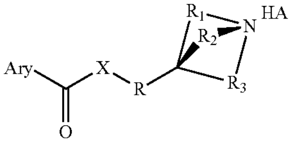

Structure 2b

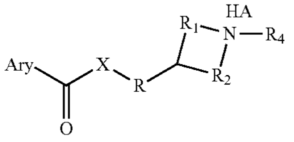

Structure 2c

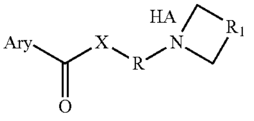

-continued

Structure 2d

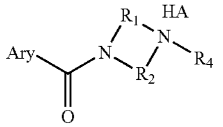

wherein, R represents a branched or straight chain $-(CH_2)_n-$, wherein n=0, 1, 2, 3, 4, 5, 6, 7, 8, 9, 10 . . . , in $-(CH_2)_n-$, any $CH_2$ may be replaced with O, S, CH═CH, C≡C, $CHR_6$, $CR_6R_7$, aryl or heteroaryl residues, or other ring systems; $R_1$ represents a branched or straight chain, $-(CH_2)_n-$, wherein a=0, 1, 2, 3, 4, 5, 6, 7, 8, 9, 10 . . . , in $-(CH_2)_n-$, any $CH_2$ may be replaced with O, S, CH═CH, C≡C, $CHR_6$, $CR_6R_7$, aryl or heteroaryl residues, or other ring systems; $R_2$ represents a branched or straight chain $-(CH_2)_b-$, wherein b=0, 1, 2, 3, 4, 5, 6, 7, 8, 9, 10 . . . , in $-(CH_2)_b-$, any $CH_2$ may be replaced with O, S, CH═CH, C≡C, $CHR_6$, $CR_6R_7$, aryl or heteroaryl residues, or other ring systems; R represents a branched or straight chain, $-(CH_2)_c-$, wherein 0, 1, 2, 3, 4, 5, 6, 7, 8, 9, 10 . . . , in $-(CH_2)_c-$, any $CH_2$ may be replaced with O, S, CH═CH, C≡C, $CHR_6$, $CR_6R_7$, aryl or heteroaryl residues, or other ring systems; R represents H, one of any alkyl, alkyloxy, alkenyl, perfluoroalkyl, alkyl halide, or alkynyl residues, having 1 to 12 carbon atoms, aryl or heteroaryl moieties, wherein, any $CH_2$ may be replaced with O, S, CH═CH, C≡C, $CHR_6$, $CR_6R_7$, aryl or heteroaryl moieties, or other ring moieties; $R_5$ represents H, one of any alkyl, alkyloxy, alkenyl, perfluoroalkyl, alkyl halide, or alkynyl residues, having 1 to 12 carbon atoms, aryl or heteroaryl moieties, wherein, any $CH_2$ may be replaced with O, S, CH═CH, C≡C, $CHR_6$, $CR_7R_6$, aryl or heteroaryl moieties, or other ring moieties; $R_6$ represents H, one of any alkyl, alkyloxy, alkenyl, perfluoroalkyl, alkyl halide, or alkynyl residues having 1 to 12 carbon atoms, aryl or heteroaryl moieties, wherein, any $CH_2$ may be replaced with O, S, CH═CH, C≡C, $CHR_7$, $CR_7R_5$, aryl or heteroaryl moieties, or other ring moieties, $R_7$ represents H, one of any alkyl, alkyloxy, alkenyl, perfluoroalkyl, alkyl halide, or alkynyl residues having 1 to 12 carbon atoms, aryl or heteroaryl moieties, wherein, any $CH_2$ may be replaced with O, S, CH═CH, C≡C, $CHR_6$, $CR_6R_5$, aryl or heteroaryl moieties, or other ring moieties; X represents none, O, NH, $NR_6$, or S; Ary- in the general formula (2a, 2b, 2c, or 2 d) "Structure 2a, 2b, 2e, or 2d" are defined as same Ary- as in the general formula (1) "Structure 1"; HA represents none, HCl, HBr, HF, HI, HOAc, citric acid, or any acids which are pharmaceutically acceptable. All R, $R_1$, $R_2$, $R_3$, $R_4$, $R_5$, $R_6$, $R_7$, or $-(CH_2)_n-$ groups are branched or straight chains and may include C, H, O, Cl, Br, F, I, P, S, N or any other atoms which are pharmaceutically acceptable and may have single, double, or/and triple bonds; all R, $R_1$, $R_2$, $R_3$, $R_4$, $R_5$, $R_6$, $R_7$, or $-(CH_2)_n-$ groups may be achiral or chiral, if a group is chiral, it may have one or more chiral centers and may be a single (R) or (S) enantiomer or a mixture of (R) and (S) enantiomers.

Drug absorption, whether from the gastrointestinal tract or other sites, requires the passage of the drug in a molecular form across the barrier membrane. The drug must first dissolve, and if the drug possesses the desirable biopharmaceutical properties, it will pass from a region of high concentration to a region of low concentration across the membrane into the blood or general circulation. All biological membranes contain lipids as major constituents. The molecules that play the dominant roles in membrane formation all have phosphate-containing highly polar head groups, and, in most cases, two highly hydrophobic hydrocarbon tails. Membranes are bilayers, with the hydrophilic head groups facing outward into the aqueous regions on either side. Very hydrophilic drugs cannot pass the hydrophobic layer of membrane and very hydrophobic drugs will stay in the hydrophobic layer as part of the membrane due to their similarities and cannot enter the cytosol on the inside efficiently.

One goal of this invention is to avoid the side effects of NSAIAs by increasing the solubility of NSAIAs in gastric juice which will make it administrable orally and the penetration rate of NSAIAs through the membranes and skin barrier which will make it administrable transdermally (topical application). The most important goal of this invention is to design pro-drugs of NSAIAs that can penetrate the skin, cell membrane, especially the brain cell and nerve cell membranes, very effectively and stay the general circulation much shorter, thus they will have tens or hundreds of times more potency than the parent drugs, only a few tenths or hundredths of the normal drug dosage is needed and much less side effects will be caused. This will benefit not only transdermal drug delivery, but also any other drug delivery systems (such as oral, subcutaneous, intravenous, inhalation, and nasal) and can treat many conditions that cannot be treated by their parent drugs. These novel pro-drugs of NSAIAs have two structural features in common: they have a lipophilic portion and a primary, secondary, or tertiary amine group that exists in the protonated form (hydrophilic part) at physiological pH. Such a hydrophilic-lipophilic balance is required for efficient passage through the membrane barrier [Susan Milosovich, et al., J. Pharm. Sci., 82, 227(1993)]. The positively charged amino groups largely increase the solubility of the drugs in water. The positive charge on the amino groups of these pro-drugs will bond to the negative charge on the phosphate head group of membrane. Thus, the local concentration of the outside of the membrane or skin will be very high and will facilitate the passage of these pro-drugs from a region of high concentration to a region of low concentration. This bonding will disturb the membrane a little bit and may make some room for the lipophilic portion of the pro-drug. When the molecules of the membrane move, the membrane may "crack" a little bit due to the bonding of the pro-drug. This will let the pro-drug insert into the membrane. At pH 7.4, only about 99% of the amino group is protonated. When the amino group is not protonated, the bonding between the amino group of the prodrug and the phosphate head group of the membrane will disassociate, and the pro-drug will enter the membrane completely. When the amino group of the pro-drug flips to the other side of the membrane and thus becomes protonated, then the pro-drug is pulled into the cytosol, a semi-liquid concentrated aqueous solution or suspension. Due to the short stay in GI tract, the pro-drugs will not cause gastric mucosal cell damage. The penetration rates of the novel pro-drugs through human skin were measured in vitro by using modified Franz cells, which were isolated from human skin tissue (360-400 μm thick) of the anterior and posterior thigh areas. The receiving fluid consisted of 10 ml of 2% bovine serum albumin in normal saline and was stirred at 600 rpm. The cumulative amounts of pro-drugs and drugs entering the skin versus time were determined by a specific high-performance liquid chromatography method. Apparent flux values of the pro-drugs of NSAIAs are 0.1-50 $mg/cm^2/h$. The results suggest that the pro-drug diffuses through human skin at least a hundred times faster than do their parent drugs. The results suggest that the positive charge on the dialkyaminoethyl group has a very important role in the passage of the drug across the membrane and skin barrier.

The novel prodrugs of NSAIAs can penetrate the skin barrier, blood-brain barrier, and blood-milk barrier. The in vivo rates of penetration of pro-drugs and their parent drugs through the skin of intact rats were compared. The donor consisted of 20% pro-drugs or their parent drugs in 1 ml of ethanol applied to about 5 $cm^2$ area on the backs of rats (~200 g). After 4 hours, the rats were killed, and 5 ml of methanol was added to 1 ml of blood, 1 g of liver, 1 g of kidney, or 1 g of brain (liver, kidney or brain was washed with pH 7.2 buffer for three times) and the mixtures were homogenized. The samples were then centrifuged for 5 min and analyzed using HPLC. The results are showed in table 1-5.

Table 1. The distribution of diethylaminoethyl acetylsalicylate.acetylsalicylic acid salt (P-1) and its metabolites in rats' body tissues and plasma.

TABLE 1

| Prodrug or metabolites | Plasma | Liver | Kidney | Brain |
|---|---|---|---|---|
| P-1 | 30 ± 10 μg/ml | 15 ± 8 μg/g | 25 ± 6 μg/g | 15 ± 6 μg/g |
| Aspirin | 25 ± 8 μg/ml | 13 ± 8 μg/g | 20 ± 6 μg/g | 15 ± 5 μg/g |
| Salicylic acid | 80 ± 10 μg/ml | 30 ± 8 μg/g | 45 ± 6 μg/g | 30 ± 6 μg/g |

Table 2. The distribution of 1-piperidinepropyl 2[(2,6-dichlorophenyl)amino]benzene acetate.AcOH (P-2) and its metabolite in rats' body tissues and plasma.

TABLE 2

| Prodrug or metabolite | Plasma | Liver | Kidney | Brain |
|---|---|---|---|---|
| P-2 | 40 ± 10 μg/ml | 22 ± 8 μg/g | 20 ± 6 μg/g | 25 ± 6 μg/g |
| diclofenac | 75 ± 8 μg/ml | 25 ± 8 μg/g | 48 ± 6 μg/g | 40 ± 5 μg/g |

Table 3. The distribution of 1-pyrrolidinepropyl 2-(3-benzoylphenyl) propionate.AcOH (P-3) and its metabolite in rats' body tissues and plasma.

TABLE 3

| Prodrug or metabolite | Plasma | Liver | Kidney | Brain |
|---|---|---|---|---|
| P-3 | 35 ± 8 μg/ml | 22 ± 8 μg/g | 25 ± 6 μg/g | 20 ± 6 μg/g |
| ketoprofen | 70 ± 8 μg/ml | 32 ± 8 μg/g | 45 ± 6 μg/g | 35 ± 5 μg/g |

Table 4. The distribution of 4-piperidinemethyl 2-(3-phenoxyphenyl)propionate.AcOH (P-4) and its metabolite in rats' body tissues and plasma.

TABLE 4

| Prodrug or metabolite | Plasma | Liver | Kidney | Brain |
|---|---|---|---|---|
| P-4 | 32 ± 8 μg/ml | 20 ± 8 μg/g | 20 ± 6 μg/g | 20 ± 6 μg/g |
| fenoprofen | 80 ± 8 μg/ml | 38 ± 8 μg/g | 48 ± 6 μg/g | 45 ± 5 μg/g |

Table 5. The distribution of 3-piperidinemethyl 2-(ρ-isobutylphenyl) propionate.AcOH (P-5) and its metabolite in rats body' tissues and plasma.

TABLE 5

| Prodrug or metabolite | Plasma | Liver | Kidney | Brain |
|---|---|---|---|---|
| P-5 | 40 ± 8 μg/ml | 25 ± 8 μg/g | 30 ± 6 μg/g | 25 ± 6 μg/g |
| ibuprofen | 70 ± 8 μg/ml | 35 ± 8 μg/g | 45 ± 6 μg/g | 35 ± 5 μg/g |

Then 20% of aspirin, diclofenac, ketoprofen, fenoprofen, or ibuprofen in 1 ml of ethanol applied to about 5 $cm^2$ area on the backs of rats. After 4 hours, the rats were killed, and 5 ml of methanol was added to 1 ml of blood, 1 g of liver, 1 g of kidney, or 1 g of brain (liver, kidney or brain was washed with pH 7.2 buffer for three times) and the mixtures were homogenized. None of these drugs was found in any rat's tissues or plasma. The results show that the pro-drugs of NSAIAs can penetrate the skin barrier, blood-brain barrier, and other membrane barriers at a very high rate, but the parent NSAIAs cannot penetrate the skin barrier in a detectable amount.

The pro-drugs of the general formula (1) "Structure 1" have demonstrated anti-inflammatory, analgesic, antipyretic, and antirheumatic activity in our patents (international application Nos: PCT/IB2006/052732, PCT/IB2006/052318, PCT/IB2006/052815, PCT/IB2006/052563, PCT/IB2006/052575, PCT/IB2006/053741, PCT/IB2006/053091, PCT/IB2006/053090, PCT/IB2006/052549). We found that the pro-drugs of the general formula (2a, 2b, 2c, or 2d) "Structure 2a, 2b, 2c, or 2d", have demonstrated anti-inflammatory, analgesic, antipyretic, and antirheumatic activity. The main focuses of this invention are the new medicinal uses of the pro-drugs of NSAIAs.

The relationship between inflammation and cancer is well known. Dr. Thea D. Tlsty described in his speech (Keystone Symposia: Inflammation and Cancer, Breckenridge, Colo., USA, Feb. 27-Mar. 3, 2005) that cyclooxygenase-2 (COX-2) stimulates aromatase activity, angiogenesis, proliferation, invasion, and prostaglandin synthesis. The increase in prostaglandins leads to an inhibition of apoptosis. Aspirin and other NSAIAs inhibit COX-1 and COX-2. The overall relative risk of colorectal cancer, oesophageal cancer, ovarian cancer or other cancers is reduced in people taking long term aspirin. However, cancer cells may change their membrane structure to keep the NSAIAs from entering the cancer cells. The novel pro-drugs in this invention can penetrate any membrane barriers and can be applied topically to the outside skin area of the location of the cancer and large amounts of the pro-drugs will enter the cancer cells with very little systemic exposure.

For evaluation of anti-tumor activity of the pro-drugs of NSAIAs, human breast cancer cells (BCAP-37, 2-3 $mm^3$ of tumor tissue was used in each mouse) were subcutaneously xenografted into nude mice (BALE, 12 groups, 7 mice each group). After 14 days, the tumors were growing to the size of 50±10 $mm^3$ (0.05 ml). Then 30 μl of 5% (equal to 1.5 mg of the pro-drugs) diethylaminoethyl acetylsalicylate.acetylsalicylic acid salt (P-1, in acetone); 1-piperidinepropyl 2[(2,6-dichlorophenyl)amino]benzene acetate.AcOH (P-2, in water), 1-pyrrolidinepropyl 2-(3-benzoylphenyl) propionate.AcOH (P-3, in water), 4-piperidinemethyl 2-(3-phenoxyphenyl)propionate.AcOH (P-4, in water), 3-piperidinemethyl 2-(ρ-isobutylphenyl) propionate.AcOH (P-5, in water), diethylaminoethyl 1-(p-chlorobenzoyl)-5-methoxy-2-methylindole 3-acetate.AcOH (P-11, in water), 2-(4-morpholinyl)ethyl (Z)-5-fluoro-2-methyl-1-[(4-methylsulfinyl)phenylmethylene]-1H-indene-3-acetate.AcOH (P-12, in water), diethylaminoethyl 2-(2,4-dichlorophenoxy)benzeneacetate.AcOH (P-19, in water), diethylaminoethyl 2-(8-methyl-10, 11-dihydro-11-oxodibenz(b,f)oxepin-2-yl)propionate.AcOH (P-37, in water), 1-pyrrolidinepropyl 2-[[(3-(trifluoromethyl)phenyl)amino]benzoate.AcOH (P-48, in water), 4-N,N-dimethylaminobutyryloxy-2-methyl-N-2-pyridinyl-2H,1,2-benzothiazine-3-carb oxamide 1,1-dioxide.HCl (P-51, in acetone) was topically applied to the human breast cancer cells-implanted area (near the front leg) every 8 hours. At day 42, the tumors sizes are shown in table 6 and table 7.

Table 6, the tumors sizes and the weights of the control group and the drug-treated groups of nude mice at day 42.

TABLE 6

| | Pro-drug | | | | | |
|---|---|---|---|---|---|---|
| | Control | P-1 | P-2 | P-3 | P-4 | P-5 |
| Size ($mm^3$) | 800 ± 100 | 150 ± 50 | 180 ± 50 | 200 ± 50 | 180 ± 50 | 190 ± 50 |
| Weight | 22 ± 2 | 22 ± 3 | 22 ± 2 | 21 ± 3 | 22 ± 3 | 23 ± 2 |

Table 7, the tumors sizes and the weights of the drug-treated groups of nude mice at day 42.

TABLE 7

| | Pro-drug | | | | | |
|---|---|---|---|---|---|---|
| | P-11 | P-12 | P-19 | P-37 | P-48 | P-51 |
| Size ($mm^3$) | 210 ± 100 | 250 ± 50 | 280 ± 50 | 250 ± 50 | 290 ± 50 | 390 ± 50 |
| Weight | 21 ± 2 | 23 ± 3 | 21 ± 2 | 23 ± 3 | 22 ± 3 | 23 ± 2 |

In the second anti-tumor experiment, human colon cancer cells (LS174J, 2-3 $mm^3$ of tumor tissue was used in each mouse) were subcutaneously xenografted into nude mice (BALB). After 7 days, the tumors were growing to the size of 55±10 $mm^3$ (0.055 ml). Then about 30 μl of 5% (equal to 1.5 mg of the pro-drugs) diethylaminoethyl acetylsalicylate.acetylsalicylic acid salt (P-1, in acetone); 1-piperidinepropyl 2[(2,6-dichlorophenyl)amino]benzene acetate.AcOH (P-2, in water), 1-pyrrolidinepropyl 2-(3-benzoylphenyl) propionate.AcOH (P-3, in water), 4-piperidinemethyl 2-(3-phenoxyphenyl)propionate.AcOH (P-4, in water), 3-piperidinemethyl 2-(ρ-isobutylphenyl) propionate.AcOH (P-5, in water), diethylaminoethyl 1-methyl-5-(4-methylbenzoyl)-1H-pyrrole-2-acetate.AcOH (P-13, in water), 2-(4-morpholinyl)ethyl 2-amino-3-benzoylbenzeneacetateAcOH (P-16, in water), diethylaminoethyl 2-(10,11-dihydro-10-oxodibenzo(b,f)thiepin-2-yl)propionate.AcOH (P-36), diethylaminoethyl 2-[(2,3-dimethylphenypamino]benzoate.AcOH (P-46, in water), diethylaminoethyl 2-[(2,6-dichloro-3-methylphenyl)amino] benzoate.AcOH (P47, in water), N-(2-thiazoyl)-4-N,N-dimethylaminobutyryloxy-2-methyl-2H,1,2-benzothiazine-3-car boxamide 1,1-dioxide.HCl (P-52, in acetone) was topically applied to the human colon cancer cells-implanted area (near the front leg) every 8 hours. At day 30, the tumors sizes are shown in table 8 and table 9.

Table 8, the tumors sizes and the weights of the control group and the drug-treated groups of nude mice at day 30.

TABLE 8

| | Pro-drug | | | | | |
|---|---|---|---|---|---|---|
| | Control | P-1 | P-2 | P-3 | P-4 | P-5 |
| Size ($mm^3$) | 1300 ± 300 | 420 ± 100 | 480 ± 180 | 500 ± 150 | 480 ± 120 | 390 ± 110 |
| Weight | 21 ± 2 | 22 ± 3 | 22 ± 2 | 21 ± 3 | 22 ± 3 | 23 ± 2 |

Table 9, the tumors sizes and the weights of the drug-treated groups of nude mice at day 30.

TABLE 9

| | Pro-drug | | | | | |
|---|---|---|---|---|---|---|
| | P-13 | P-16 | P-36 | P-46 | P-47 | P-52 |
| Size ($mm^3$) | 610 ± 200 | 550 ± 150 | 480 ± 180 | 650 ± 250 | 490 ± 150 | 690 ± 250 |
| Weight | 21 ± 2 | 23 ± 3 | 21 ± 2 | 23 ± 3 | 22 ± 3 | 23 ± 2 |

The results show that the pro-drugs of NSAIAs have very strong anti-tumor activity and have none or very little side effects.

The hypoglycemic effect of salicylates was first observed over 100 years ago by German physicians (Edmund J. Hengesh, Principles of medicinal chemistry, 4th ed., pg 591, Williams & Wilkins, 1995). Salicylates enhance glucose-stimulated insulin secretion and inhibits glucogenesis from lactate and alanine (H. F. Woods, et al., Clin. Exp. Pharmacol Physiol., 1, 534(1974). Certain salicylates decrease plasma levels of free fatty acids, triglycerides, and cholesterol. Because elevated levels of plasma-free fatty acids inhibit glucose utilization, a decrease in their concentration could contribute to the hypoglycemic action. Unfortunately, the large doses (5 g daily) of salicylates are necessary to maintain adequate control of blood sugar levels and blood lipid levels. At these dosage levels, numerous side effects, such as gastric irritation, nausea, vomiting, and tinnitus, occur frequently. The novel pro-drugs in this invention have very high skin and membrane penetration rates. They can reach the "site of action" very fast and the pharmacologic effect and the clinical response of these pro-drugs are increased greatly, then much smaller (only hundredths to tenths of the parent drug dosage needed) drug dosage will be needed and much less side effects will be caused.

The pro-drugs in this invention lower blood glucose levels in rat models (SLAC/GK, type 2 diabetes, n=7). 50% acetone solution of diethylaminoethyl acetylsalicylate.acetylsaficylic acid salt (P-1, in acetone); 4-acetamidophenyl salicylyldimethylaminobutyrate.HCl (P-6), diethylaminoethyl 5-(2,4-difluorophenyl) acetylsalicylate.5-(2,4-difluorophenyl) acetylsalicylic acid salt (P-8), diethylaminoethyl salicylsalicylate.AcOH (P-9), diethylaminoethyl salicylate.AcOH (P-10), diethylaminoethyl 5-acetamido-acetylsalicylate (P-58), diethylaminoethyl acetylsalicylsalicylate. acetylsalicylsalicylic acid salt (P-59), diethylaminoethyl acetylsalicylsalicylate. acetylsalicylsalicylsalicylic acid salt (P-60) (equal to of 20 mg/kg of NSAIAs) were administered transdermally to the backs (about 1.5 $cm^2$) of rats (fur was shaved) once per day (at 8 am) for 5 weeks. The blood glucose levels were measured once every 3 days at 4 pm (no asting) from the second week to the fifth week. The results f are shown in table 10. The blood lipid levels were measured at the end of the fifth week. The results are shown in table 11.

Table 10. Anti-Diabetes Activity of the Pro-Drugs of NSAIAs

TABLE 10

| | | Prodrug | | | | | | | | |
|---|---|---|---|---|---|---|---|---|---|---|
| | | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
| Diabetic | Baseline | 15.6 ± 3 | 16.1 ± 3 | 16.7 ± 4 | 17.1 ± 3 | 16.5 ± 4 | 15.8 ± 3 | 17.1 ± 3 | 16.3 ± 3 | 15.5 ± 3 |
| rats | Average | 15.9 ± 3 | 6.5 ± 1 | 8.5 ± 2 | 8.1 ± 1 | 8.4 ± 1 | 8.2 ± 1 | 8.4 ± 1 | 8.7 ± 1 | 8.6 ± 1 |
| Normal | Baseline | 6.5 ± 1 | 6.4 ± 1 | 6.8 ± 1 | 7.1 ± 1 | 6.5 ± 1 | 6.8 ± 1 | 6.9 ± 1 | 7.2 ± 1 | 6.6 ± 1 |
| rats | Average | 6.6 ± 1 | 6.3 ± 1 | 6.5 ± 1 | 6.8 ± 1 | 6.7 ± 1 | 6.9 ± 1 | 7.1 ± 1 | 7.3 ± 1 | 7.5 ± 1 |

The results showed that the pro-drug s of NSAIAs lowered blood glucose levels in diabetes rat models very effectively and did not affect the blood glucose levels of normal rats. The most interesting thing is that the blood glucose levels of the rats still stayed at normal levels (7-8 mmol/L, no fasting) after the treatment was stopped for 30 days. This means that the pro-drugs not only control blood glucose levels, but also may cure diabetes.

Table 11. Blood Lipid-Lowering Activity of the Pro-Drugs of NSAIAs

TABLE 11

| | | Prodrug | | | | | | | | |
|---|---|---|---|---|---|---|---|---|---|---|
| | | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
| cholesterol | Baseline | 7.6 ± 0.5 | 7.7 ± 0.4 | 7.3 ± 0.5 | 7.6 ± 0.6 | 7.7 ± 0.5 | 7.1 ± 0.5 | 7.8 ± 0.5 | 7.6 ± 0.6 | 7.3 ± 0.6 |
| (total) | Average | 7.9 ± 0.5 | 4.0 ± 0.3 | 4.7 ± 0.4 | 5.3 ± 0.3 | 4.8 ± 0.4 | 4.9 ± 0.4 | 5.4 ± 0.4 | 5.1 ± 0.3 | 5.2 ± 0.3 |
| Cholesterol | Baseline | 1.4 ± 0.1 | 1.4 ± 0.2 | 1.3 ± 0.1 | 1.6 ± 0.2 | 1.3 ± 0.1 | 1.6 ± 0.2 | 1.3 ± 0.1 | 1.6 ± 0.2 | 1.3 ± 0.2 |
| (HDL) | Average | 1.3 ± 0.1 | 1.5 ± 0.2 | 1.3 ± 0.2 | 1.5 ± 0.2 | 1.4 ± 0.2 | 1.5 ± 0.1 | 1.4 ± 0.2 | 1.6 ± 0.2 | 1.5 ± 0.2 |
| Triglycerides | Baseline | 5.2 ± 0.7 | 5.9 ± 0.5 | 6.3 ± 0.5 | 5.6 ± 0.6 | 5.7 ± 0.5 | 6.6 ± 0.6 | 5.3 ± 0.5 | 5.6 ± 0.5 | 5.7 ± 0.6 |
| | Average | 5.5 ± 0.6 | 1.5 ± 0.2 | 2.3 ± 0.2 | 2.1 ± 0.2 | 2.6 ± 0.2 | 2.9 ± 0.2 | 2.4 ± 0.2 | 2.9 ± 0.2 | 2.5 ± 0.2 |

The results showed that the pro-drug s of NSAIAs lowered blood lipid levels (total cholesterol and triglycerides) in diabetes rat models very effectively and did not affect HDL levels.

The pH of stomach juice is 1-3. The negative charge on the phosphate head group of membrane is neutralized by the proton and the positive charge on the amino groups of these pro-drugs cannot bond to the phosphate head group of membranes, then the pro-drugs cannot pass through the wall of the stomach and will not hurt or upset the stomach. The pH of the duodenum is about 5-7 and the pro-drugs can pass through the mucosa of duodenum. The pancreas is nearby and large amount of the pro-drugs will enter there before going to the liver, kidneys, and the general circulation where the drug will be metabolized, so only very low dose of these pro-drugs are needed and very few and low side effects will be caused. The 20% acetone solution of diethylaminoethyl acetylsalicylate.acetylsalicylic acid salt (P-1, in acetone); 4-acetamidophenyl salicylyldimethylaminobutyrate.HCl (P-6), diethylaminoethyl 5-(2,4-difluorophenyl) acetylsalicylate.5-(2,4-difluorophenyl) acetylsalicylic acid salt (P-8), diethylaminoethyl salicylsalicylate.AcOH (P-9), diethylaminoethyl salicylate.AcOH (P-10), diethylaminoethyl 5-acetamido-acetylsalicylate (P-58), diethylaminoethyl acetylsalicylsalicylate. acetylsalicylsalicylic acid salt (P-59), diethylaminoethyl acetylsalicylsalicylate. acetylsalicylsalicylsalicylic acid salt (P-60) (equal to of 15 mg/kg of NSAIAs) were mixed with food and were orally administered to the rats (SLAC/GK, type 2 diabetes, n=7) with food every day for 5 weeks. The blood glucose levels were measured once every 3 days at 3 pm (no fasting) from the second week to the fifth week. The results are shown in table 12. The blood lipid levels were measured at the end of the fifth week. The results are shown in table 13.

Table 12. Anti-Diabetes Activity of the Pro-Drugs of NSAIAs

TABLE 12

| | | Prodrug | | | | | | | | |
|---|---|---|---|---|---|---|---|---|---|---|
| | Control mmol/L | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
| Diabetic | Baseline | 15.3 ± 3 | 16.5 ± 3 | 16.1 ± 4 | 16.1 ± 3 | 16.5 ± 4 | 15.6 ± 3 | 17.0 ± 3 | 15.3 ± 3 | 16.5 ± 3 |
| rats | Average | 15.6 ± 3 | 6.5 ± 1 | 7.5 ± 2 | 7.3 ± 1 | 7.6 ± 1 | 7.8 ± 1 | 8.4 ± 1 | 8.6 ± 1 | 7.9 ± 1 |
| Normal | Baseline | 6.6 ± 1 | 6.3 ± 1 | 6.5 ± 1 | 7.0 ± 1 | 6.3 ± 1 | 6.7 ± 1 | 6.9 ± 1 | 7.5 ± 1 | 6.8 ± 1 |
| rats | Average | 6.5 ± 1 | 6.5 ± 1 | 6.4 ± 1 | 6.8 ± 1 | 6.6 ± 1 | 6.9 ± 1 | 7.2 ± 1 | 7.3 ± 1 | 7.3 ± 1 |

The results showed that the pro-drug s of NSAIAs lowered blood glucose levels in diabetic rat models very effectively and did not affect the blood glucose levels of normal rats when the pro-drugs were taken orally and the dosages are much smaller than that of the parent drugs.

Table 13. Blood Lipid-Lowering Activity of the Pro-Drugs of NSAIAs

TABLE 13

| | | Prodrugs | | | | | | | | |
|---|---|---|---|---|---|---|---|---|---|---|
| | | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
| Cholesterol | Baseline | 7.8 ± 0.6 | 7.7 ± 0.4 | 7.5 ± 0.4 | 7.4 ± 0.6 | 7.9 ± 0.5 | 7.6 ± 0.5 | 7.9 ± 0.5 | 7.7 ± 0.6 | 7.5 ± 0.5 |
| (total) | Average | 8.1 ± 0.5 | 4.1 ± 0.3 | 4.7 ± 0.4 | 5.1 ± 0.3 | 5.3 ± 0.4 | 5.2 ± 0.5 | 4.9 ± 0.4 | 5.1 ± 0.3 | 5.0 ± 0.3 |
| Cholesterol | Baseline | 1.7 ± 0.1 | 1.5 ± 0.1 | 1.8 ± 0.1 | 1.4 ± 0.2 | 1.5 ± 0.1 | 1.6 ± 0.2 | 1.8 ± 0.1 | 1.9 ± 0.2 | 1.5 ± 0.2 |
| (HDL) | Average | 1.5 ± 0.1 | 1.6 ± 0.2 | 1.4 ± 0.2 | 1.3 ± 0.2 | 1.4 ± 0.2 | 1.7 ± 0.1 | 1.6 ± 0.2 | 1.8 ± 0.2 | 1.6 ± 0.2 |
| Triglycerides | Baseline | 5.5 ± 0.6 | 5.7 ± 0.5 | 5.9 ± 0.5 | 6.2 ± 0.7 | 5.8 ± 0.6 | 5.7 ± 0.6 | 5.9 ± 0.5 | 5.4 ± 0.6 | 6.2 ± 0.5 |
| | Average | 5.8 ± 0.6 | 1.4 ± 0.2 | 1.8 ± 0.2 | 1.8 ± 0.2 | 2.7 ± 0.2 | 2.6 ± 0.2 | 2.8 ± 0.2 | 2.7 ± 0.2 | 2.5 ± 0.2 |

The results showed that the pro-drug s of NSAIAs lowered blood lipid levels (total cholesterol and triglycerides) in diabetic rat models very effectively when the pro-drugs were taken orally and the dosages are much smaller than that of the parent drugs.

The pro-drugs in this invention lower blood glucose levels in mouse models (SLAC:NOD-IDDM, type 1 diabetes, n=7). 20% acetone solution of diethylaminoethyl acetylsalicylate.acetylsalicylic acid salt (P-1, in acetone); 4-acetamidophenyl salicylyldimethylaminobutyrate.HCl (P-6), diethylaminoethyl 5-(2,4-difluorophenyl) acetylsalicylate.5-(2,4-difluorophenyl) acetylsalicylic acid salt (P-8), diethylaminoethyl salicylsalicylate.AcOH (P-9), diethylaminoethyl salicylate.AcOH (P-10), diethylaminoethyl 5-acetamido-acetylsalicylate (P-58), diethylaminoethyl acetylsalicylsalicylate. acetylsalicylsalicylic acid salt (P-59), diethylaminoethyl acetylsalicylsalicylate. acetylsalicylsalicylsalicylic acid salt (P-60) (equal to of 20 mg/kg of NSAIAs) were administered transdermally to the backs (about 1 $cm^2$) of mice (fur was shaved) once per day (at 8 am) for 7 weeks. The blood glucose levels were measured once every 3 days at 3 pm (no fasting) from the fourth week to the seventh week. The results are shown in table 14.

Table 14. Anti-Diabetes (Type I) Activity of the Pro-Drugs of NSAIAs

TABLE 14

| | Prodrug | | | | | | | | |
|---|---|---|---|---|---|---|---|---|---|
| | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
| Baseline | 28.6 ± 5 | 26.1 ± 5 | 27.7 ± 4 | 29.1 ± 5 | 26.5 ± 4 | 25.8 ± 3 | 27.1 ± 3 | 24.3 ± 3 | 25.5 ± 3 |
| Average | 32.9 ± 5 | 6.5 ± 1 | 9.5 ± 2 | 9.1 ± 1 | 9.4 ± 1 | 8.2 ± 1 | 7.9 ± 1 | 8.7 ± 1 | 8.6 ± 1 |

The results showed that the pro-drugs of NSAIAs lowered blood glucose levels in diabetic (type I) mouse models very effectively.

Eighteen Chinese White rabbits weighing between 3.0 and 3.5 kg (aged 6-7 months) were selected and divided into three groups (control, P-1 and P-10 groups, n=6). One hour before the experiment, thrombi were made by aspirating venous blood (1 ml) into a sterilized bottle to clot. To avoid fragmentation and slow lysis, the autologous blood clots were stabilized in temperature-controlled (70° C.) distilled water for 10 min. After anesthesia, the femoral veins were exposed and distally isolated, and autologous blood clots (0.05 g/kg) were injected through an indwelling catheter (20GA), which had been placed in the femoral vein isolated earlier. 50% acetone solution of diethylaminoethyl acetylsalicylate.acetylsalicylic acid salt (P-1, in acetone, 15 mg/kg) and diethylaminoethyl acetylsalicylsalicylate.acetylsalicylsalicylic acid salt (P-59, 15 mg/kg) were topically applied to the back of the rabbits. After 2 days, rabbits were euthanized with an excessive intravenous injection of sodium amobarbital (60 mg/kg). The lungs and hearts were isolated to observe whether thrombi were present in the pulmonary arteries. The lungs were immersed in 10% formalin for 24 h. Consecutive transverse sections along the obstructed pulmonary arteries were paraffin-embedded and stained with hematoxylin-eosine. In the control group, platelet thrombus and mixed thrombus surrounded the infused clots, which were present in large-sized vessels as well and stretched the vessel walls in both proximal and distal directions. There was excessive proliferation of endothelial cells and fibrocytes in these vessels. Additionally, there was acute pulmonary congestion. In the P-1 and P-59 groups, both lung tissue and vascular walls were normal. The results showed that thrombotic activity and that embolization-associated thrombus propagation can be prevented by these pro-drugs of NSAIAs. These pro-drugs can be very useful for preventing and treating blood clots—a major cause of strokes, heart attacks and organ transplant rejection.

The pro-drugs in this invention can help heal wounds and soften and shrink scars from cuts and burns in rabbit models. The average scar area of the pro-drugs treated rabbits is only a third of that of the control rabbits from same size cut wounds in the Chinese white rabbit model and the scars are as soft as normal unscarred tissues.

COX-1 and COX-2 play a very important role in animal immune-responses. NSAIAs inhibite COX-1 and COX-2. The pro-drugs of NSAIAs in this invention may be very useful for treating psoriasis, discoid lupus erythematosus, systemic lupus erythematosus (SLE), and other autoimmune diseases. Heavy suspensions of Malassezia [Rosenberg, E. W., et al., Mycopathologia, 72, 147-154 (1980)] were applied to the shaved skin on the backs of the Chinese white rabbits (n=4×6) twice (at 7 am and 7 pm) per day for 2 weeks, lesions similar to psoriasis resulted. Then a 5% aqueous solution of 3-piperidinemethyl 2-(ρ-isobutylphenyl) propionate.AcOH (P-5), diethylaminoethyl 1-methyl-5-(4-methylbenzoyl)-1H-pyrrole-2-acetate.AcOH (P-13), diethylaminoethyl 5-(4-Chlorobenzoyl)-1,4-dimethyl-1H-pyrrole-2-acetate.AcOH (P-14), diethylaminoethyl 1,8-diethyl-1,3,4,9-tetrahydropyrano-[3,4-b]indole-1-acetate.AcOH (P-15), diethylaminoethyl 2-amino-3-(4-bromobenzoyl)benzeneacetate.AcOH (P-17) diethylaminoethyl 3-chloro-4-(2-propenyloxy)benzeneacetate.AcOH (P-18), diethylaminoethyl 1-(4-chlorobenzoyl-5-methoxy-2-methyl-1H-indole-3-acetoxyacetate.AcOH (P-20), diethylaminoethyl 4-(4-chlorophenyl)-2-phenyl-5-thiazoleacetate.AcOH (P-21), diethylaminoethyl 3-(4-chlorophenyl)-1-phenyl-1H-pyrazole-4-acetate.AcOH (P-22) were applied to the same areas 3 hours (10 am and 10 pm) after the application of heavy suspensions of Malassezia (7 am and 7 pm). 10 days after the application of these pro-drugs, the lesions were resolved. but the condition of the control mice were getting worse.

For evaluation of anti-lupus erythematosus activity, 5% diethylaminoethyl acetylsalicylate.acetylsalicylic acid salt (P-1, in acetone, 30 mg/kg) or 3-piperidinemethyl 2-(ρ-isobutylphenyl) propionate.AcOH (P-5, in water, 30 mg/kg) were topically applied to the skin on the backs of mice (MRL/LPR, n=5×3) with discoid lupus erythematosus and systemic lupus erythematosus twice per day. After 6 weeks, all skin lesions and lupus nephritis were resolved in the pro-drug treated mice, but the condition of the control mice were getting worse.

These results suggest that these pro-drugs of NSAIAs are very promising agents for the treatment of psoriasis, discoid lupus erythematosus, systemic lupus erythematosus (SLE), multiple sclerosis (MS), and other autoimmune diseases in human.

The pathogenesis of cell death in amyotrophic lateral sclerosis (ALS) may involve glutamate-mediated excitotoxicity, oxidative damage, and apoptosis. Cyclooxygenase-2, present in spinal neurons and astrocytes, catalyzes the synthesis of prostaglandin E2. Prostaglandin E2 stimulates glutamate release from astrocytes, whereas cyclooxygenase-2 also plays a key role in the production of pro-inflammatory cytokines, reactive oxygen species, and free radicals. Treatment with a selective cyclooxygenase-2 inhibitor, celecoxib, markedly inhibited production of prostaglandin E2 in the spinal cords of ALS mice. Celecoxib treatment significantly delayed the onset of weakness and weight loss and prolonged survival by 25%. Spinal cords of treated ALS mice showed significant preservation of spinal neurons and diminished astrogliosis and microglial activation (Merit. E. Cudkowicz, et al., Annals of neurology, 52, 771-778, 2002). These results suggest that cyclooxygenase-2 inhibition may benefit ALS patients. The pro-drugs of NSAIAs in this invention can penetrate skin and nerve cell membrane barriers in very high rates (most NSAIAs cannot penetrate nerve cells effectively) and can be administered transdermally without hurting the GI tract, so these pro-drug are very promising agents for the treatment of multiple sclerosis (MS), Crohn's disease, and other autoimmune diseases, amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders.

Inflammatory mechanisms have been proposed as important mediators in the pathogenetic cascade of Alzheimer's disease (McGeer P L, McGeer E G. The inflammatory response system of brain implications for the therapy of Alzheimer and other neurodegenerative diseases. Brain Res. Rev., 1995; 21: 195-218). In the study by in't Veld et al. (the New England Journal of Medicine, 2001; 345, 1515), they followed almost 7000 person at risk of Alzheimer's disease for nearly seven years. Their results suggested that NSAIAs can reduce the relative risk for those whose cumulative use of NSAIAs was at least two years and two or more years before the onset of dementia. If the neuroprotective capacity of NSAIAs ceases in the years just before the onset of dementia, then these compounds would offer no protection against progression among most persons with the prodromal stage of diseases. We believe that the reason for this is that the tissues around the damaged nerve cells will form scars to protect the nerve cells from damaging farther. Most of NSAIAs have very low brain-blood and nerve cell barriers penetration rate and cannot penetrate the scar barrier. These pro-drugs in this invention have very high skin, blood-brain, nerve cell membrane, and scar barriers penetration rates and are very promising agents for the treatment of Alzheimer's disease, Parkinson's diseases, and other progressive neurodegenerative diseases.

These pro-drugs may help the patients with a spinal cord injury in which the healing is stopped by the protected scars around the injured spinal cord. Most NSAIAs cannot penetrate the scar barrier in a therapeutic effective amount, but the pro-drugs in this invention can penetrate the scar barrier, have anti-inflammatory activity, and can help wound healing.

NSAIAs are not very effective for treatment of the conditions described above or have serious side effects because they cannot penetrate the cell membrane, especially the brain cells and nerve cells, very effectively and stay the general circulation too long, thus most of drugs will be metabolized by intestinal mucosa, liver, kidney, and lung before they reach the "site of action." This situation not only produces very low pharmacologic effect, but also causes toxic burden on intestinal mucosa, liver, kidneys, lungs, and other parts of the body. These pro-drugs in this invention penetrate skin, brain-blood, brain cells, nerve cells and other membranes barriers very well and they have hundreds of times more potency than the parent drugs, only a few tenths or hundredths of the normal drug dosage is needed and much less side effects will be caused. This will benefit not only transdermal drug delivery, but also any other drug delivery system (such as oral, subcutaneous, intravenous, inhalation, and nasal) and can treat many conditions better than they can be treated by their respective parent drugs and even some conditions which cannot be treated by their respective parent drugs.

The compounds of the general formula (1, 2a, 2b, 2c, or 2d) "Structure 1, 2a, 2b, 2c, or 2d" indicated above can be prepared from NSAIAs, by reaction with N,N'-Dicyclohexylcarbodiimide N, N'-Diisopropylcarbodiimide or other coupling reagents to form anhydrides, then react with suitable alcohols, thiols, or amines.

The compounds of the general formula (1, 2a, 2b, 2c, or 2d) "Structure 1, 2a, 2b, 2c, or 2d" indicated above can be prepared from metal salts, organic base salts, or immobilized base salts of NSAIAs with suitable halide compounds.

Transdermal therapeutic application systems of a compound of the general formula (1, 2a, 2b, 2c, or 2d) "Structure 1, 2a, 2b, 2c, or 2d" or a composition comprising of at least one compound of the general formula (1, 2a, 2b, 2c, or 2d) "Structure 1, 2a, 2b, 2e, or 2d" as an active ingredient, can be used for treating any NSAIAs-treatable conditions and any conditions described in this invention in humans or animals. These systems can be a bandage or a patch comprising of one active substance-containing matrix layer and an impermeable backing layer. The most preferable system is an active substance reservoir, which has a permeable bottom facing the skin. By controlling the rate of release, this system enables NSAIAs to reach constantly optimal therapeutic blood levels to increase effectiveness and reduce the side effects of NSAIAs. These systems can be worn on the wrist, ankle, arm, leg, or any part of body.

Advantageous Effects

NSAIAs are not very effective for treatment of the conditions described in this invention or have serious side effects because they cannot penetrate the cell membrane, especially the brain cells and nerve cells, very effectively and stay in the general circulation too long, thus most of drugs will be metabolized by intestinal mucosa, liver, kidneys, and lungs before they reach the "site of action." This situation not only produces very low pharmacologic effect, but also causes toxic burden on intestinal mucosa, liver, kidneys, lungs and any other parts of the body. These pro-drugs in this invention penetrate skin, brain-blood, brain cells, nerve cells, scars and other membranes barriers very well, and they have hundreds of times more potency than the parent drugs, only a few tenths or hundredths of the normal drug dosage is needed and much less side effects will be caused. This will benefit not only transdermal drug delivery, but also any other drug delivery system (such as oral, subcutaneous, intravenous, inhalation, and nasal) and can treat many conditions that cannot be treated by their parent drugs. These pro-drugs can be administered not only transdermally, but also orally (they will not hurt stomach because they cannot penetrate the wall of the stomach) for any type of medical treatment and should avoid most of the side effects of NSAIAs, most notably GI disturbances such as dyspepsia, gastroduodenal bleeding, gastric ulcerations, and gastritis. Another great benefit of transdermal administration of these pro-drugs is that administering medication, especially to children, will be much easier.

DESCRIPTION OF DRAWINGS

FIG. 2A depicts the chemical structure of Structure 2a.

BEST MODE

Figure 1:
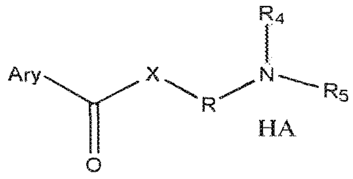
FIG. 1 depicts the chemical structure of Structure 1.
Figure 2A:
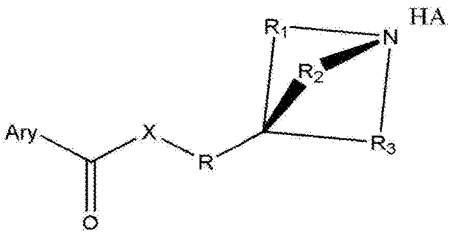
Figure 2B:
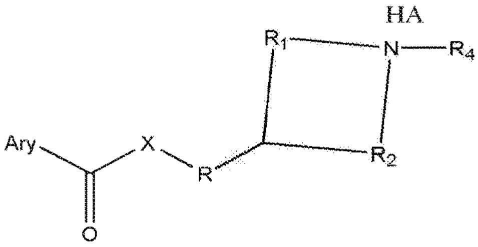
FIG. 2B depicts the chemical structure of Structure 2b.
Figure 2C:
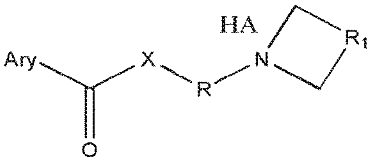
FIG. 2C depicts the chemical structure of Structure 2c.
Figure 2D:
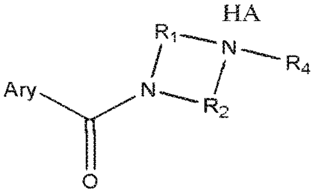
FIG. 2D depicts the chemical structure of Structure 2d.

Preparation of Diethylaminoethyl Acetylsalicylate.Acetylsalicylic Acid Salt 180 g of 2-acetylsalicyclic acid was dissolved in 1000 ml of chloroform. The mixture was cooled to 5° C. 103 g of 1,3-Dicyclohexylcarbodiimide was added into the mixture. The mixture is stirred for 2 h at RT. The solid waste is removed by filtration and washed with chloroform (3×300 ml). 59 g of diethylaminoethanol were added into the reaction mixture. The mixture was stirred for 3 hours at RT. The organic solution was evaporated off. After drying, it yielded 220 g of the desired product (96%). Elementary analysis: $C_{24}H_{29}NO_8$; MW: 459.18. Calculated % C, 62.73; H, 636; N, 3.05; O, 27.86. Found % C, 62.70; H, 6.40; Cl, N, 3.01; O, 27.90.

MODE FOR INVENTION

Preparation of 1-piperidinepropyl 2[(2,6-dichlorophenyl)amino]benzene acetate.AcOH 31.8 g (0.1 mol) of sodium 2[(2,6-dichlorophenyl)amino] benzene acetate was suspended in 180 ml of chloroform. 28.6 g (0.1 mol) of 1-piperidinepropyl bromide.HBr was added into the mixture and the mixture was stirred for 5 hours at RT. The mixture is washed with 5% $Na_2CO_3$ (1×300 ml) and water (3×100 ml). The mixture is dried over anhydrous $Na_2SO_4$. Sodium sulfate was removed by filtration and washed with chloroform (3×50 ml). 6 g of acetic acid was added into the solution. The solution is concentrated in vacuo to 100 ml. Then 300 ml of hexane was added into the solution. The solid product was collected by filtration and washed with hexane (3×100 ml). After drying, it yielded 40 g of the desired product (86%). Elementary analysis: $C_{24}H_{30}Cl_2N_2O_4$; MW: 481.43 Calculated % C, 59.88; H, 6.28; Cl, 14.73; N, 5.82; O, 13.29. Found % C, 59.83; H, 6.32; Cl, 14.71; N, 5.79; O, 13.35.

Preparation of 3-piperidinemethyl 2-(ρ-isobutylphenyl) propionate.AcOH 60 g of Polymer-bound triethylamine (3 mmol/g, 100-200 mesh) was suspended in 500 ml of chloroform. 20.6 g (0.1 mol) of 2-(ρ-isobutylphenyl) propionic acid was added into the mixture with stirring. 39 g (0.15 mol) of 3-piperidinemethyl bromide.HBr was added into the mixture and the mixture was stirred for 10 hours at RT. The polymer is removed by filtration and washed with acetone (3×50 ml). 300 ml of 5% $Na_2CO_3$ was added into the solution with stirring. The mixture is stirred for 30 min. The chloroform solution is washed with water (3×100 ml) and dried over $Na_2SO_4$. Sodium sulfate is removed by filtration and washed with chloroform (3×100 ml). 6 g of acetic acid was added into the mixture. The solution is concentrated in vacuo to 100 ml. Then 300 ml of hexane was added into the solution. The solid product was collected by filtration and washed with hexane (3×100 ml). After drying, it yielded 35 g of the desired product (96%). Elementary analysis: $C_{21}H_{33}NO_4$; MW: 363.49 Calculated % C, 69.39; H, 9.15; N, 3.85; O, 17.61. Found % C, 69.35; H, 9.18; N, 3.83; O, 17.64.

INDUSTRIAL APPLICABILITY

The pro-drugs of the general formulas (1, 2a, 2b, 2c, or 2d) "Structure 1, 2a, 2b, 2c, or 2d" are superior to NSAIAs. They can be used medicinally in treating any NSAIAs-treatable conditions in humans or animals. They can be used also for treating and preventing diabetes (type I & II), abnormal blood glucose and lipid levels, stroke, heart attack, and other heart and vascular diseases Alzheimer's diseases, Parkinson's diseases and other neurodegenerative diseases, psoriasis, discoid lupus erythematosus, systemic lupus erythematosus (SLE), autoimmune hepatitis, scleroderma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, and pulmonary fibrosis, multiple sclerosis (MS), Crohn's disease, and other autoimmune diseases, amyotrophic lateral sclerosis (ALS), oculopharyngeal muscular dystrophy (OPMD), myotonic dystrophy (MD), Duchenne muscular dystrophy (DMD), polymyositis (PM), dermatomyositis (DM), inclusion body myositis (IBM), and other muscle disorders, hemorrhoids, inflamed hemorrhoids, post irradiation (factitial) proctitis, chronic ulcerative colitis, cryptitis, other inflammatory conditions of the anorectum, and pruritus ani, prostatitis, prostatocystitis, autoimmune liver inflammation, autoimmune kidney inflammation, vein inflammation and other inflammations, spinal cord injuries, scars, breast cancer, colon-rectum cancer, oral cancer, lung and other respiratory system cancers, skin cancer, uterus cancer, genital cancer, urinary organs cancers, leukemia and other blood and lymph tissues cancers and other cancers, and many other conditions. These pro-drugs can be administered transdermally without the help of skin penetration enhancers.

The invention claimed is:

1. A compound selected from

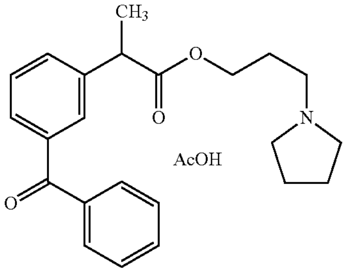 [SMILES: "AcOH" ; CC(C(=O)OCCCN1CCCC1)c1cccc(C(=O)c2ccccc2)c1]

3-(pyrrolidin-1-yl)propyl 2-(3-benzoylphenyl)propanoate.AcOH,

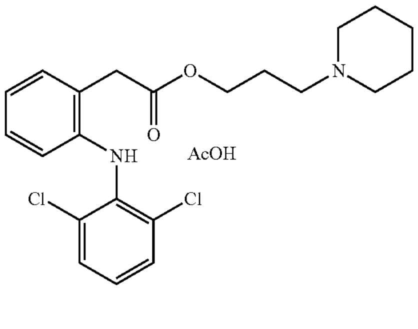 [SMILES: "AcOH" ; O=C(Cc1ccccc1Nc1c(Cl)cccc1Cl)OCCCN1CCCCC1]

3-(piperidin-1-yl)propyl 2-(2-((2,6-dichlorophenyl) amino)phenyl)acetate.AcOH,

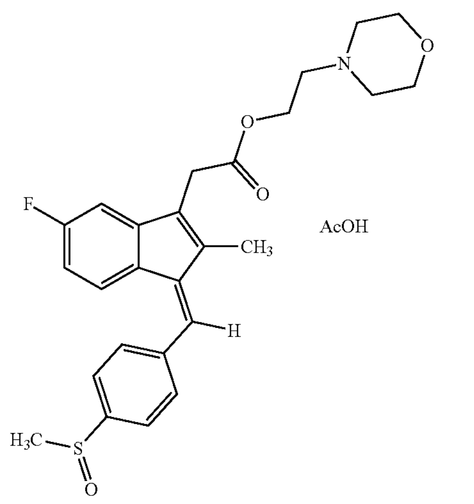 [SMILES: "AcOH" ; CC1=C(CC(=O)OCCN2CCOCC2)c2cc(F)ccc2/C1=C\c1ccc(S(C)=O)cc1]

2-morpholinoethyl (Z)-2-(5-fluoro-2-methyl-1-(4-(methylsulfinyl)benzylidene)-1H-inden-3-yl)acetate.AcOH,

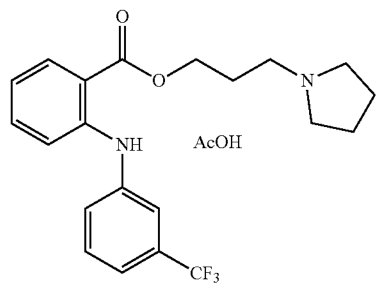 [SMILES: "AcOH" ; O=C(OCCCN1CCCC1)c1ccccc1Nc1cccc(C(F)(F)F)c1]

3-(pyrrolidin-1-yl)propyl 2-((3-(trifluoromethyl)phenyl)amino)benzoate.AcOH, and

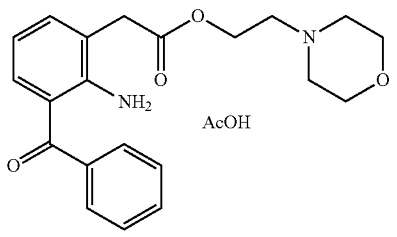 [SMILES: "AcOH" ; Nc1c(CC(=O)OCCN2CCOCC2)cccc1C(=O)c1ccccc1]

2-morpholinoethyl 2-(2-amino-3-benzoylphenyl)acetate.AcOH.

2. A pharmaceutical composition comprising a compound and a pharmaceutically acceptable excipient, wherein the compound is selected from

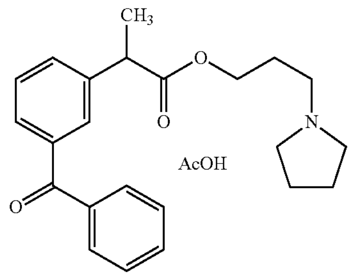 [SMILES: "AcOH" ; CC(C(=O)OCCCN1CCCC1)c1cccc(C(=O)c2ccccc2)c1]

3-(pyrrolidin-1-yl)propyl 2-(3-benzoylphenyl)propanoate.AcOH,

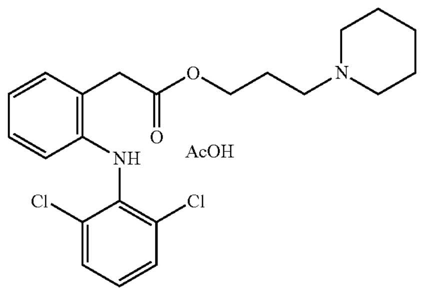 [SMILES: "AcOH" ; O=C(Cc1ccccc1Nc1c(Cl)cccc1Cl)OCCCN1CCCCC1]

3-(piperidin-1-yl)propyl 2-(2-((2,6-dichlorophenyl)amino)phenyl)acetate.AcOH,

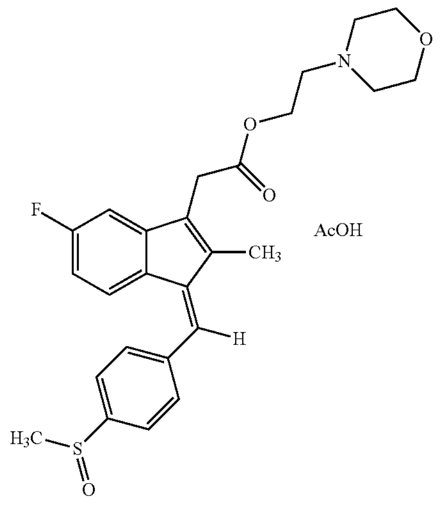 [SMILES: "AcOH" ; CC1=C(CC(=O)OCCN2CCOCC2)c2cc(F)ccc2/C1=C\c1ccc(S(C)=O)cc1]

2-morpholinoethyl (Z)-2-(5-fluoro-2-methyl-1-(4-(methylsulfinyl)benzylidene)-1H-inden-3-yl)acetate.AcOH,

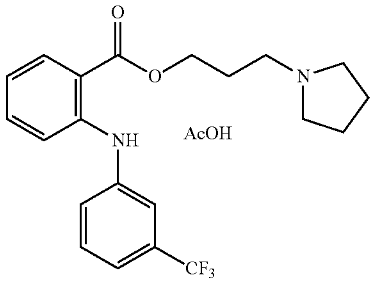 [SMILES: "AcOH" ; O=C(OCCCN1CCCC1)c1ccccc1Nc1cccc(C(F)(F)F)c1]

3-(pyrrolidin-1-yl)propyl 2-((3-(trifluoromethyl)phenyl)amino)benzoate.AcOH, and

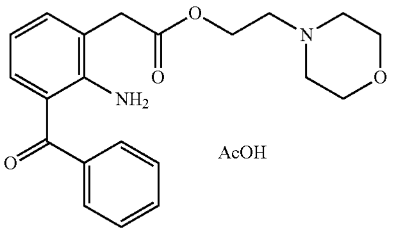 [SMILES: "AcOH" ; Nc1c(CC(=O)OCCN2CCOCC2)cccc1C(=O)c1ccccc1]

2-morpholinoethyl 2-(2-amino-3-benzoylphenyl)acetate.AcOH.

3. The pharmaceutical composition of claim 2, wherein the pharmaceutical composition is formulated in the form of a solution, spray, emulsion, pill, or tablet.

4. The pharmaceutical composition of claim 2, which is for transdermal therapeutic application.

5. The pharmaceutical composition of claim 2, comprising water and a compound selected from

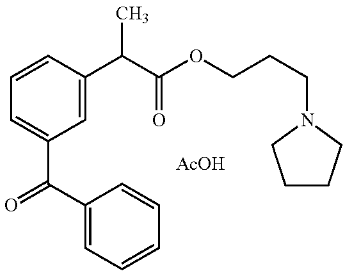 [SMILES: "AcOH" ; CC(C(=O)OCCCN1CCCC1)c1cccc(C(=O)c2ccccc2)c1]

3-(pyrrolidin-1-yl)propyl 2-(3-benzoylphenyl)propanoate.AcOH,

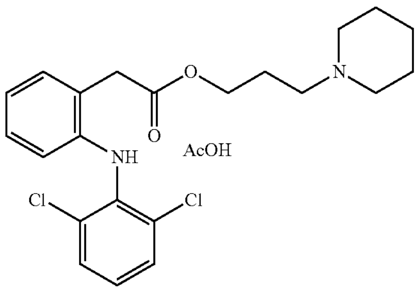 [SMILES: "AcOH" ; O=C(Cc1ccccc1Nc1c(Cl)cccc1Cl)OCCCN1CCCCC1]

3-(piperidin-1-yl)propyl 2-(2-((2,6-dichlorophenyl)amino)phenyl)acetate.AcOH,

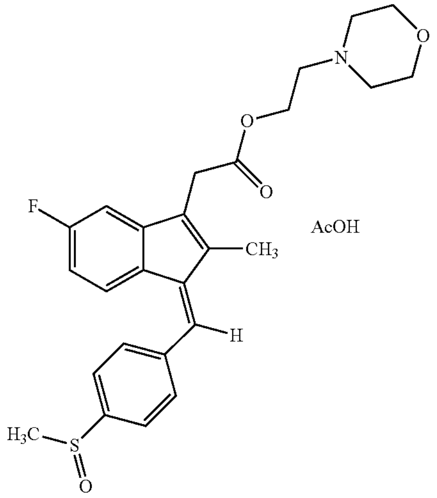 [SMILES: "AcOH" ; CC1=C(CC(=O)OCCN2CCOCC2)c2cc(F)ccc2/C1=C\c1ccc(S(C)=O)cc1]

2-morpholinoethyl (Z)-2-(5-fluoro-2-methyl-1-(4-(methylsulfinyl)benzylidene)-1H-inden-3-yl)acetate.AcOH,

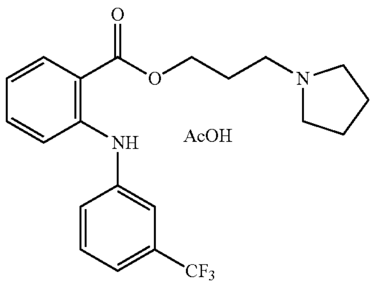 [SMILES: "AcOH" ; O=C(OCCCN1CCCC1)c1ccccc1Nc1cccc(C(F)(F)F)c1]

3-(pyrrolidin-1-yl)propyl 2-((3-(trifluoromethyl)phenyl)amino)benzoate.AcOH, and

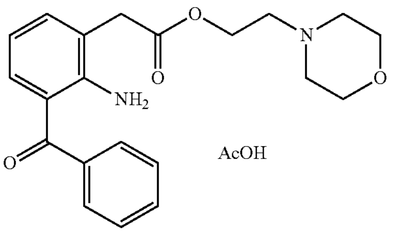 [SMILES: "AcOH" ; Nc1c(CC(=O)OCCN2CCOCC2)cccc1C(=O)c1ccccc1]

2-morpholinoethyl 2-(2-amino-3-benzoylphenyl)acetate.AcOH.

6. A transdermal therapeutic application system comprising a compound according to claim 1 and an active substance reservoir.

7. The transdermal therapeutic application system according to claim 6, further comprising a bandage or a patch comprising one active substance-containing matrix layer and an impermeable backing layer.

8. The transdermal therapeutic application system according to claim 6, wherein the active substance reservoir comprises a permeable bottom facing the skin.

9. A compound selected from

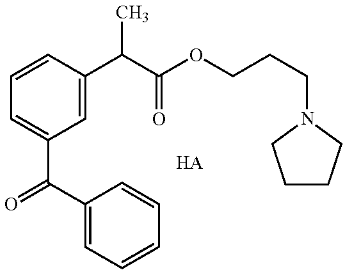

3-(pyrrolidin-1-yl)propyl 2-(3-benzoylphenyl)propanoate.HA,

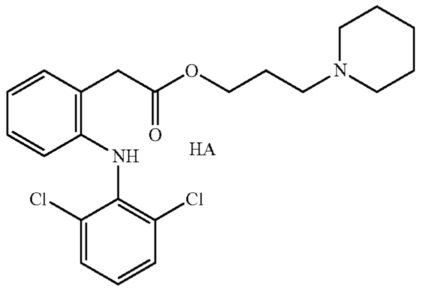

3-(piperidin-1-yl)propyl 2-(2-((2,6-dichlorophenyl)amino)phenyl)acetate.HA,

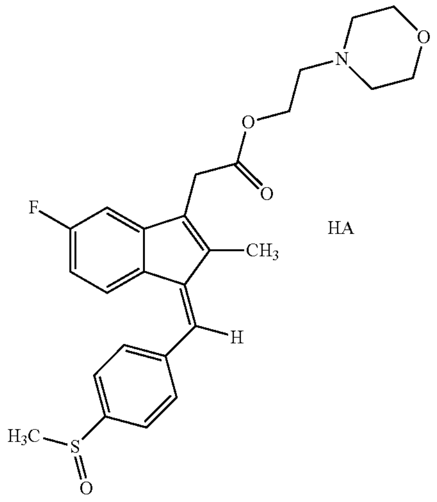 [SMILES: CC1=C(CC(=O)OCCN2CCOCC2)c2cc(F)ccc2/C1=C\c1ccc(S(C)=O)cc1 ; "HA"]

2-morpholinoethyl (Z)-2-(5-fluoro-2-methyl-1-(4-(methylsulfinyl)benzylidene)-1H-inden-3-yl)acetate.HA,

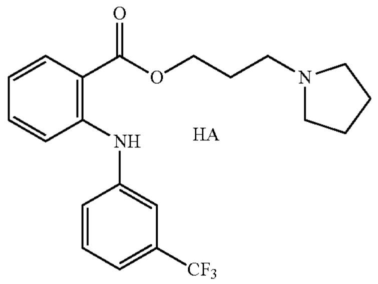 [SMILES: O=C(OCCCN1CCCC1)c1ccccc1Nc1cccc(C(F)(F)F)c1 ; "HA"]

3-(pyrrolidin-1-yl)propyl 2-((3-(trifluoromethyl)phenyl)amino)benzoate.HA, and

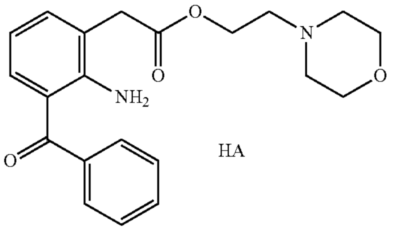 [SMILES: Nc1c(CC(=O)OCCN2CCOCC2)cccc1C(=O)c1ccccc1 ; "HA"]

2-morpholinoethyl 2-(2-amino-3-benzoylphenyl)acetate.HA, wherein HA is a pharmaceutically acceptable acid.

10. The compound according to claim 9, wherein HA is HCl, HBr, HF, HI, HOAc, or citric acid.

11. The compound according to claim 1, wherein the compound is

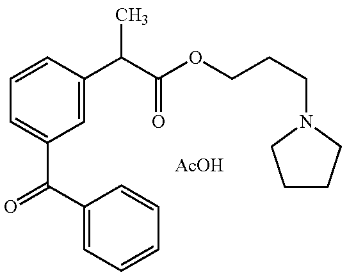 [SMILES: "AcOH" ; CC(C(=O)OCCCN1CCCC1)c1cccc(C(=O)c2ccccc2)c1]

3-(pyrrolidin-1-yl)propyl 2-(3-benzoylphenyl)propanoate.AcOH.

* * * * *